(12) United States Patent
Lin et al.

(10) Patent No.: US 8,900,879 B2
(45) Date of Patent: Dec. 2, 2014

(54) SENSOR FOR DETECTION OF A TARGET OF INTEREST

(71) Applicant: National Taiwan University, Taipei (TW)

(72) Inventors: Shiming Lin, Taipei (TW); Si-Chen Lee, Taipei (TW); Luan-Yin Chang, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 13/911,949

(22) Filed: Jun. 6, 2013

(65) Prior Publication Data

US 2013/0330813 A1 Dec. 12, 2013

Related U.S. Application Data

(63) Continuation-in-part of application No. 13/835,379, filed on Mar. 15, 2013.

(60) Provisional application No. 61/656,354, filed on Jun. 6, 2012.

(51) Int. Cl.

| | | |
|---|---|---|
| G01N 33/566 | (2006.01) | |
| G01N 33/53 | (2006.01) | |
| G01N 21/01 | (2006.01) | |
| G01N 21/82 | (2006.01) | |
| G01N 33/569 | (2006.01) | |
| G01N 21/59 | (2006.01) | |
| G01N 33/00 | (2006.01) | |
| C12M 3/00 | (2006.01) | |

(52) U.S. Cl.
CPC .......... *G01N 21/82* (2013.01); *G01N 33/56983* (2013.01); *G01N 21/59* (2013.01)
USPC ........ 436/501; 435/6.1; 435/7.72; 435/287.2; 436/86; 422/82.06

(58) Field of Classification Search
None
See application file for complete search history.

(56) References Cited

U.S. PATENT DOCUMENTS

| | | | | |
|---|---|---|---|---|
| 5,512,131 | A * | 4/1996 | Kumar et al. | 438/738 |
| 2003/0170613 | A1 * | 9/2003 | Straus | 435/5 |
| 2005/0191663 | A1 * | 9/2005 | Beattie | 435/6 |
| 2010/0323372 | A1 * | 12/2010 | Fulton et al. | 435/7.72 |
| 2011/0053794 | A1 * | 3/2011 | Zhang | 506/9 |

* cited by examiner

*Primary Examiner* — Neil N Turk
(74) *Attorney, Agent, or Firm* — Muncy, Geissler, Olds & Lowe, P.C.

(57) ABSTRACT

Embodiments of the present disclosure set forth a sensor for detecting a target of interest. One example sensor may comprise an apparatus for binding the target of interest and a draining unit for draining fluid from the apparatus. The apparatus may comprise a substrate, a material disposed on the substrate, and a probe disposed on the material and configured to bind to the target of interest. The probe is configured on the material to scatter light emitted from a light source when the target of interest is bound to the probe.

22 Claims, 20 Drawing Sheets

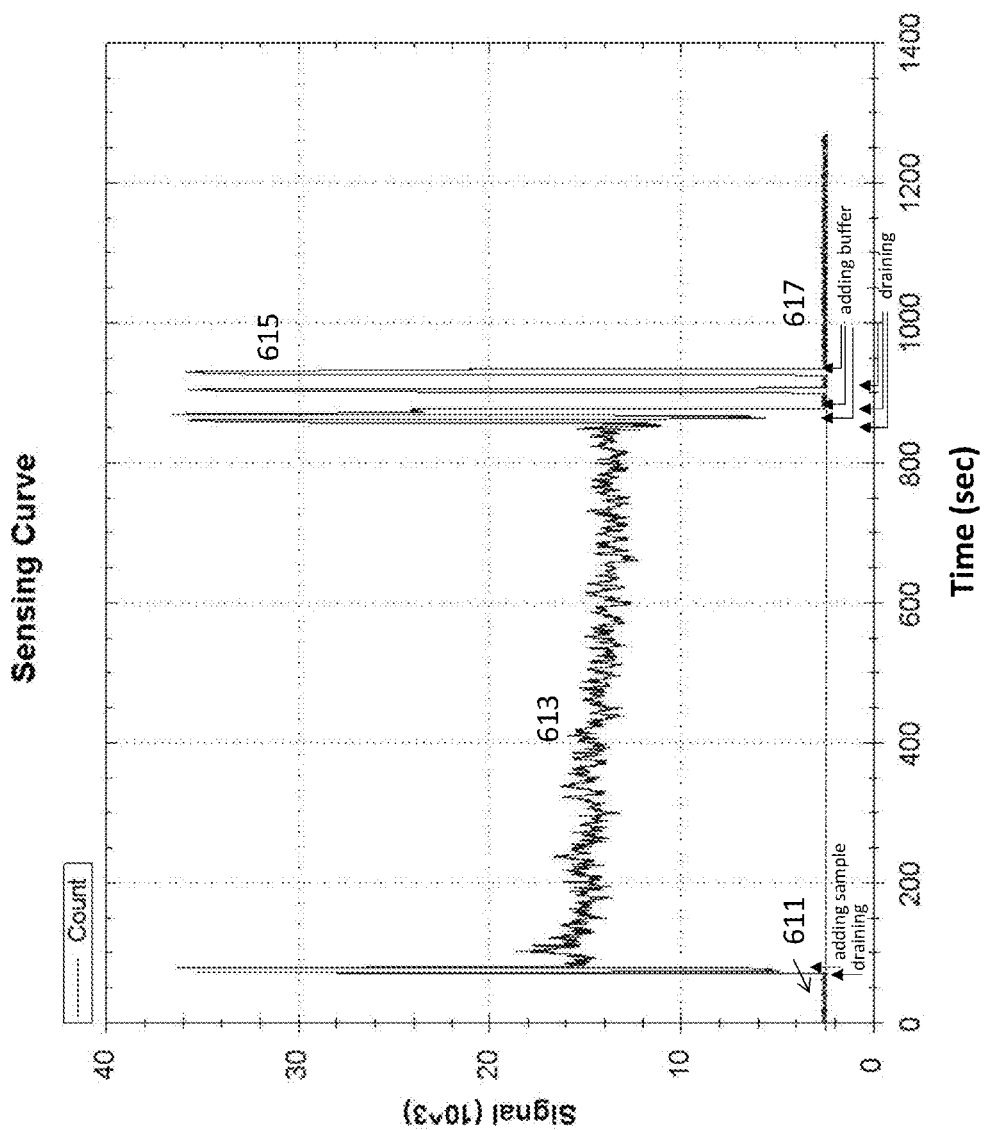

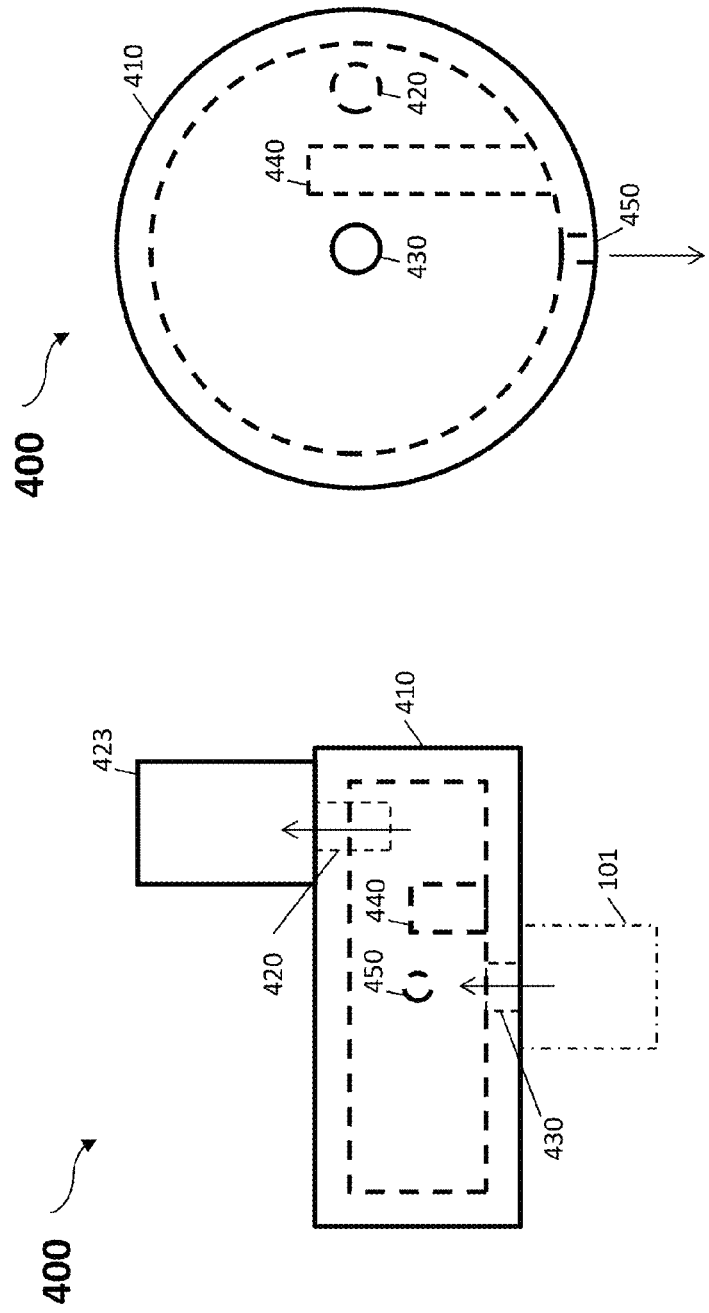

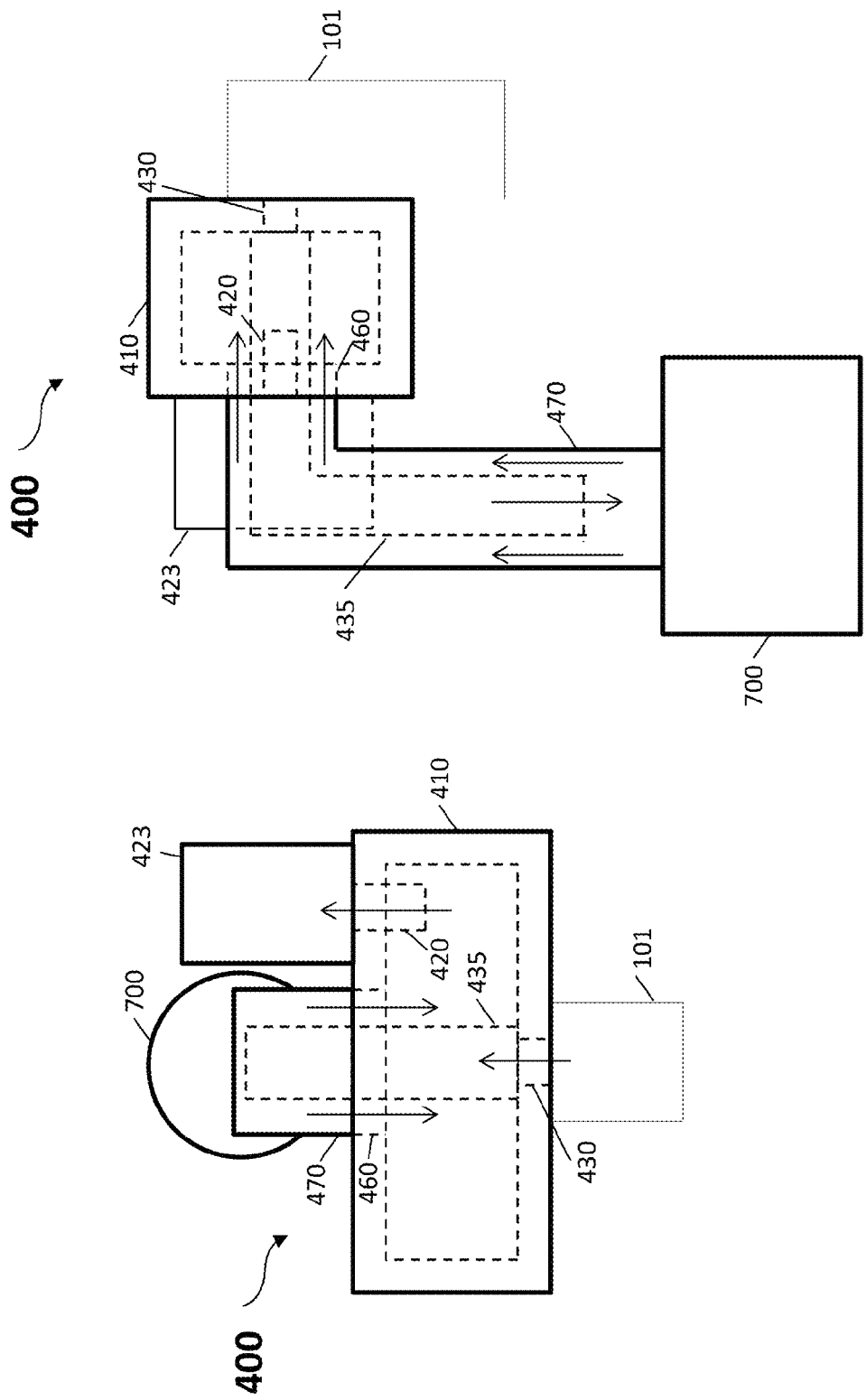

SENSOR FOR DETECTION OF A TARGET OF INTEREST

CROSS REFERENCE TO RELATED APPLICATIONS

This application is a Continuation-in-Part of co-pending Application No. 13/835,379, filed on 15 Mar. 2013, for which priority is claimed under 35 U.S.C. §120; and this application claims priority of U.S. Provisional Application No. 61/656,354 filed on 6 Jun. 2012 under 35 U.S.C. §119(e), the entire contents of all of which are hereby incorporated by reference.

BACKGROUND OF THE DISCLOSURE

A biological sensor is an analytical device for detecting a target molecule by interaction of a biomolecule with the target molecule. Compared to culturing or polymerase chain reaction (PCR), a biological sensor can detect the existence of the target molecule within a relatively short time period. Some biological sensors use chromatographic immunoassay techniques. However, these chromatographic immunoassay-based biological sensors have adoption issues. For example, most chromatographic immunoassay-based biological sensors detect antibodies which are generated by the patients after a later stage of infection/disease.

BRIEF DESCRIPTION OF THE DRAWINGS

FIG. 6B is a chart illustrating the signal strength during detection, by the sensor, of influenza B in a control sample collected from a healthy person, all arranged in accordance with embodiments of the disclosure;

FIG. 7A shows the top view of an illustrative embodiment of a draining unit of a sensor for detecting a target of interest (e.g., a biomolecule);

FIG. 7B shows the front view of the illustrative embodiment of the draining unit of a sensor for detecting a target of interest (e.g., a biomolecule) in FIG. 7A;

FIG. 8A shows the top view of another illustrative embodiment of a draining unit of a sensor for detecting a target of interest (e.g., a biomolecule);

FIG. 8B shows a side view of the illustrative embodiment of the draining unit of a sensor for detecting a target of interest (e.g., a biomolecule) in FIG. 8A;

SUMMARY

Figure 1:
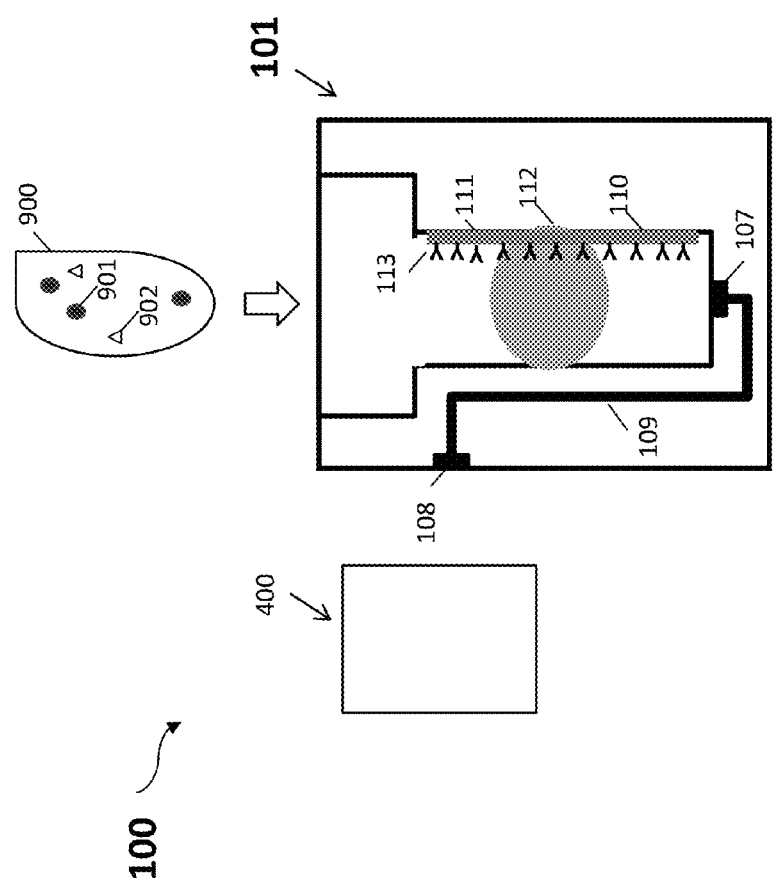
FIG. 1 shows an illustrative embodiment of a sensor for detecting a target of interest (e.g., a biomolecule)

Some embodiments of the present disclosure may generally relate to a sensor for binding a target of interest. One example sensor may comprise an apparatus for binding the target of interest and a draining unit for draining fluid from the apparatus. The apparatus may comprise a substrate, a material disposed on the substrate, and a probe disposed on the material and configured to bind to the target of interest. The probe is configured on the material to scatter light emitted from a light source when the target of interest is bound to the probe.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

In this disclosure, the term "probe" generally refers to a substance (e.g., a biomolecule) that is capable of binding to a target of interest (e.g., a biomolecule). For example, a probe may have a binding affinity for the target of about 100 piconewtons (pN) to about 500 pN. Nonlimiting examples of probes include antibodies, antibody fragments that retain the ability to bind to the target of interest, nucleic acids (e.g., DNA, RNA, aptamers), antigens, and enzymes. In a sensor as described herein, a single probe that recognizes a single target of interest, or two or more probes that recognize a single target or multiple targets of interest may be used.

The term "target" generally refers to any molecule that is detectable with a sensor as described herein. A target may include, but is not limited to, a biomolecule. Examples of targets that are detectable in the sensors described herein include, but are not limited to, biomolecules (for example, virus, proteins, nucleic acids, carbohydrates, lipids), and other types of molecules (e.g., small molecules) such as, haptens, and toxins. In some embodiments, the target is a biomolecule that is present in a bodily fluid and/or tissue.

In some embodiments, a sensor for detecting a target of interest (e.g., a biomolecule) includes a light source, a container, and a light receiver having a light detector that generates an electrical signal that is proportionate to the amount of light received by the light receiver. At least one inner surface of the container includes probes immobilized on a material that is disposed on the container surface. The light source is configured to generate light that passes through the container and eventually to the light detector. The light may be of a specific wavelength. Depending on the target to be detected, the specific wavelength may be changed accordingly. The specific wavelength may be determined by any technical feasible approaches. In some embodiments, the specific wavelength is determined by scanning the target with the visible light spectrum or UV light spectrum. The maximum absorption wavelength of the target in the visible light spectrum may be the specific wavelength. For example, any of enterovirus 71, influenza A virus, and influenza B virus has a maximum absorption at about 560 nanometer (nm) wavelength in the visible light spectrum and has a relatively greater absorption at about 280 nm wavelength in the ultra-violet spectrum. Adenovirus has a maximum absorption at about 340 nm wavelength in the visible light spectrum and has a relatively greater absorption at about 280 nm wavelength in the ultra-violet spectrum. If the target is present and bound to the probes, light is scattered as it passes through the container, amplifying the signal and resulting in a higher level of light reaching the light receiver, and a larger magnitude electrical signal generated by the light detector.

In some embodiments, the light source may generate visible light or ultra-violet light. A light filter may be placed between the light source and the container so that the light entering the container has a specific wavelength. Alternatively, the light filter may be placed between the container and the light detector so that the light entering the light detector has a specific wavelength. Alternatively, some optical elements (e.g., slit, grating, mirror and a linear charge-coupled device) may be placed between the container and the light detector to produce monochromatic light having a specific wavelength from the visible light that passed through the container, and allow the monochromatic light to enter the light detector. Alternatively, the light source may be a monochromatic light source.

In some embodiments, the container includes a substrate, a material disposed on the substrate and one or more probe(s) disposed on the material. The probe is immobilized on the material. The probe may be a biological substance, for example, an antibody, an antibody fragment, a nucleic acid, an aptamer, an antigen or an enzyme, or any substance that is capable of binding to a target of interest in a manner such that light scattering occurs when the target is bound to the probe to a greater degree than when no target is bound. The material is compatible with the probe and the probe can be immobilized on the material. The material may be, for example, a metal such as gold, silver, copper and nickel. The substrate may be composed of any composition that is technically feasible for the material to be disposed thereon, and that does not interfere with detection of a target of interest as described herein. Some examples of suitable substrates may include, without limitation, glass, metal, silicon or polymers.

The material includes a pattern configured to enhance the light scattering when the target is bound to the probe. In some embodiments, the pattern itself is configured to scatter light when the light travels through the pattern. In some embodiments, the pattern may be a film coated on the substrate. In some other embodiments, the coated film may be annealed. The annealing makes the surface of the coated film becomes uneven. The uneven surface may enhance the scattering of the light passing through the container, and may provide an increase in the surface area available for the deposition of the probe.

In some embodiments, the pattern may be a metal rod array disposed on the substrate. The three dimensional property of the metal rod array may also provide an increase in the surface area available for the deposition of the probe. The size of a metal rod in the metal rod array is associated with the specific wavelength set forth above. The length of any metal rod is neither a multiple nor a factor of the specific wavelength. The width of any metal rod is neither a multiple nor a factor of the specific wavelength. The distance between two adjacent rods is neither a multiple nor a factor of the specific wavelength.

The probe is disposed or immobilized on the material through one or more chemical bonds (e.g., covalent bond) with the material. The probe may form a "lock and key" relationship with the target to be detected by the sensor. For example, the probe may be DNA, RNA, a protein, an antibody, an antibody fragment, an aptamer, an antigen, or an enzyme. In some embodiments, the probe is an antibody and the target is an antigen to which the antibody binds.

A sample potentially including the target is introduced into the sensor and then flows over the probe. If the target exists in the sample, the amount of photons passing through the container before the sample is introduced into the sensor may be different than the amount of photons passing through the container after the sample is introduced into the sensor because the target coupled with the probe scatters photons. If the target does not exist in the sample, the amount of photons passing through the container remains substantially the same because there is no bound target to scatter photons. In some embodiments, the amount of photons absorbed by the sample is higher in the presence of bound target than in the absence of the target, resulting in a difference in the light signal detected when the target is present and the light signal detected when the target is absent.

In some embodiments, a method for making a sensor is disclosed. The method includes providing a material which includes a pattern configured to scatter light or enhance a light scattering associated with the target of interest, and increase the surface area available for binding with the probes, disposing the material on a substrate and disposing the probes configured to interact with the target of interest on the material.

In some embodiments, the material is a film. The substrate may be cleaned before the material is disposed on the substrate. In some embodiments, before the material is disposed on the substrate, an adhesion layer is disposed on the substrate first. Then the material is disposed on the adhesion layer. The adhesion layer may be chromium.

In some other embodiments, the material is an annealed film which has an uneven surface pattern. The material may be annealed at a temperature from about 300 degrees Celsius (° C.) to about 500° C. after the material is disposed on the adhesion layer.

In some other embodiments, the material includes a rod array pattern. A photoresist is coated on the substrate and a photolithography process is performed to form the rod array. The size of each rod in the rod array and the distance between two adjacent rods are associated with at least one of the specific wavelength, the size of the probe, and the size of the target of interest.

In some embodiments, a method for detecting a target of interest with a sensor described herein is disclosed. The sensor includes a light source, a container and a light detector. The container includes a substrate, a material disposed on the substrate and a probe configured to interact with the target of interest. The probe is disposed and immobilized on the material. The method includes transmitting light from the light source through the container and obtaining a first signal based on the light received by a light detector of the sensor.

The method also includes placing a sample that potentially includes the target of interest in the sensor and obtaining a second signal based on the light received by the light detector after the sample is placed in the container. The method further includes comparing the first signal and the second signal and determining whether the target exists in the sample based on the comparison.

FIG. 1 is an illustrative embodiment of a sensor 100 for detecting a target of interest. The sensor 100 includes a container 101. The container forms an apparatus for binding a target of interest, and includes a material 111 disposed on a substrate 110 (e.g., one or more walls of the container) and probes 113 that are capable of binding to the target disposed on the material. A light 112 is transmitted from a light source of the sensor 100 to a light receiver of the sensor 100 through the container 101. The probes 113 disposed on the material 111 are configured in the path of the light emitted by the light source. The probes 113 are configured such that light passing over the apparatus is scattered when the target of interest is bound to the probes 113.

A solution that does not contain the target, such as a buffer solution, is introduced into the container 101. The light 112 is configured to pass through the container 101 in a first time slot and is received by the light receiver. The light receiver further includes a photodiode detector configured to generate a first electronic signal based on the amount of the light 112 that is received by the light receiver in the first time slot. The light receiver further includes a processor for processing the first electronic signal.

A sample 900 potentially including the target of interest 901 is then introduced into the container 101. A predetermined amount of time is allowed to lapse so that if the target of interest 901 exists in the sample 900, the target of interest 901 may bind to the probes 113 on the material 111. After the predetermined period of time has lapsed, introduced sample 900 in the container 101, including impurities 902, is removed from the container 101 by a draining unit 400 through a first hole 107, a passage 109 and a second hole 108, without breaking the bond between the target of interest 901 and the probes 113. Subsequently, the container 101 is rinsed with a buffer solution for a predetermined number of times. For example, fresh buffer solution may be repeatedly injected into and pumped out from the container 101 several times.

Light scattering that occurs when target molecules are bound to the probes 113 on the apparatus will be detected, indicating presence of the target 901 in the sample 900. The light 112 is configured to pass through the container 101 in a second time slot and is received by the light receiver. The photodiode detector of the light receiver is configured to generate a second electronic signal based on the amount of the light that is received by the light receiver in the second time slot. The processor of the light receiver is configured to further process the second electronic signal. If the strength of the second signal differs significantly from the first signal, the processor determines that the target of interest exists in the sample. For example, if the second signal is significantly stronger than the first signal, the processor determines that the target of interest is present in the sample.

Figure 2A:
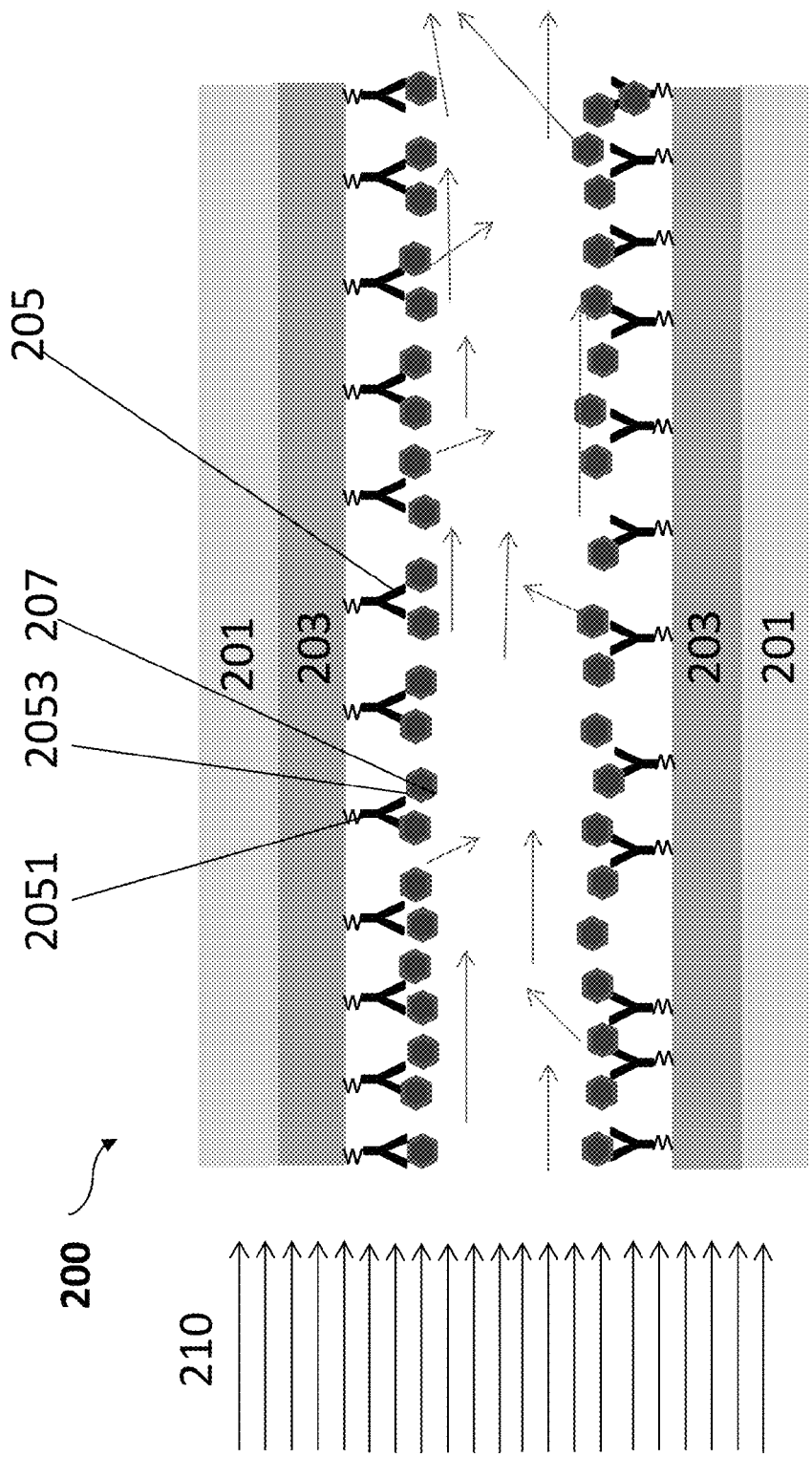
FIG. 2A shows an illustrative embodiment of a container of a sensor for detecting a target of interest (e.g., a biomolecule)

FIG. 2A shows an illustrative embodiment of an apparatus for binding a target of interest. The apparatus 200 includes a substrate 201, a film 203 disposed on the substrate and a probe 205 disposed on the film 203. The thickness of the film 203 may be, for example, a substantially even thickness of about 5 nm to about 200 nm. A first surface 2051 of the probe 205 is disposed on the material 203. A second surface 2053 of the probe 205 having a binding affinity for the target 207 is configured such that it is available to couple with the target 207 when the target 207 is present. The probes 205 are configured on the film 203 such that light 210 (shown as arrow in FIG. 2A) is scattered when the target 207 binds to the second surface 2053 of probes 205.

Figure 2B:
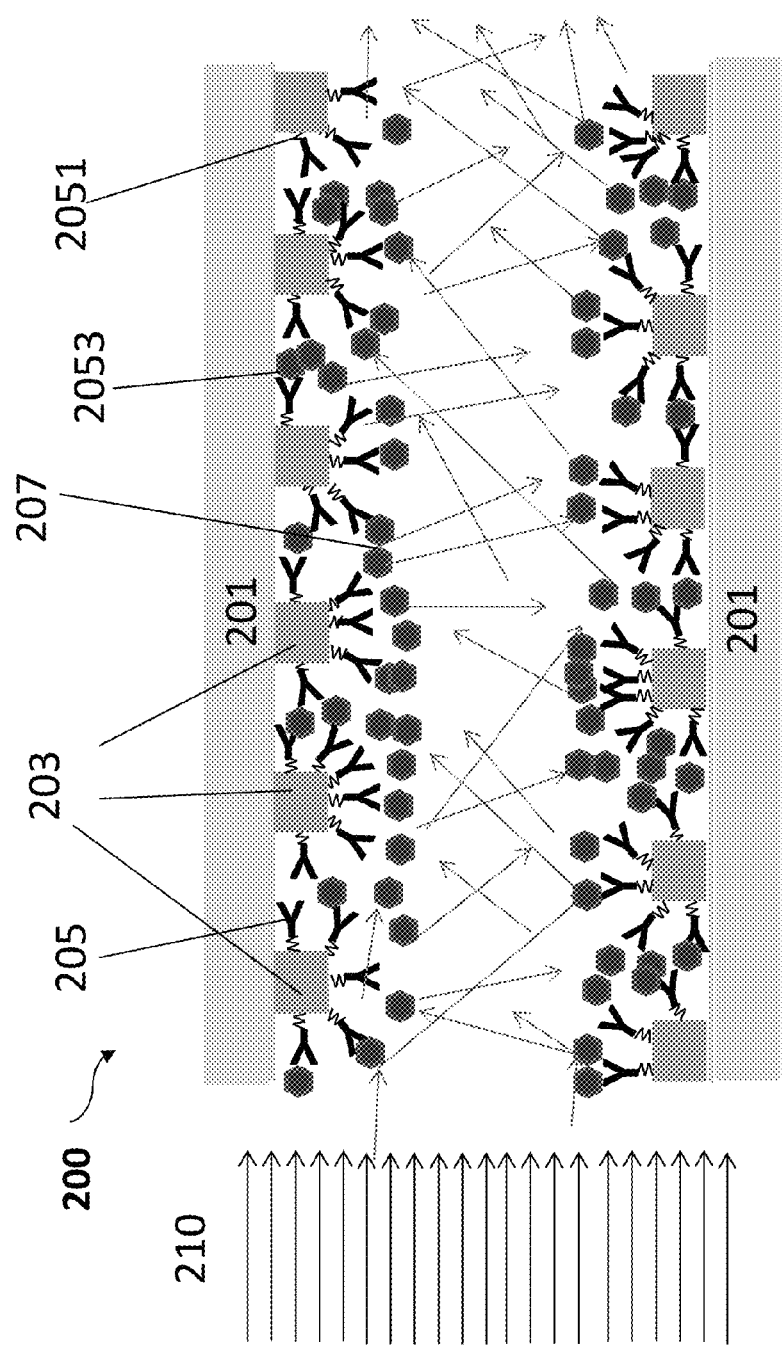
FIG. 2B shows another illustrative embodiment of a container of a sensor for detecting a target of interest (e.g., biomolecule)

FIG. 2B shows an illustrative embodiment of an apparatus for binding a target of interest. The apparatus 200 includes a substrate 201, a rod array 203 disposed on the substrate and a probe 205 disposed on the rod array 203. The width and the length of any rod in the rod array 203 and the distance between two adjacent rods are associated with at least one of the wavelength of light transmitted from a light source of the sensor, the size of the probe 205 and the target of interest 207. The wavelength is specific to a target of interest 207. The distance between two adjacent rods is also associated with such wavelength. In some embodiments, the width, the length and the distance are all neither a multiple of the wavelength, nor a factor of the wavelength. In some embodiments, the rod of the rod array 203 may have a length from 200 to 900 nm, a width from 200 to 900 nm and a height from 15 to 1500 nm. The distance between each rod in the rod array may be from 200 to 900 nm. In some embodiments, the rod of the rod array may have a length of approximately 500 nm, a width of approximately 500 nm and a height of about 100 nm, and the distance between each rod may be approximately 500 nm. A first surface 2051 of the probe 205 is disposed on the rod array 203. A second surface 2053 of the probe 205 having a binding affinity for the target 207 is configured such that it is available to couple with the target 207 when the target 207 is present. The probes 205 are configured on the rod array 203 such that light 210 (shown as arrow in FIG. 2B) is scattered when the target 207 binds to the second surface 2053 of probes 205.

Figure 2C:
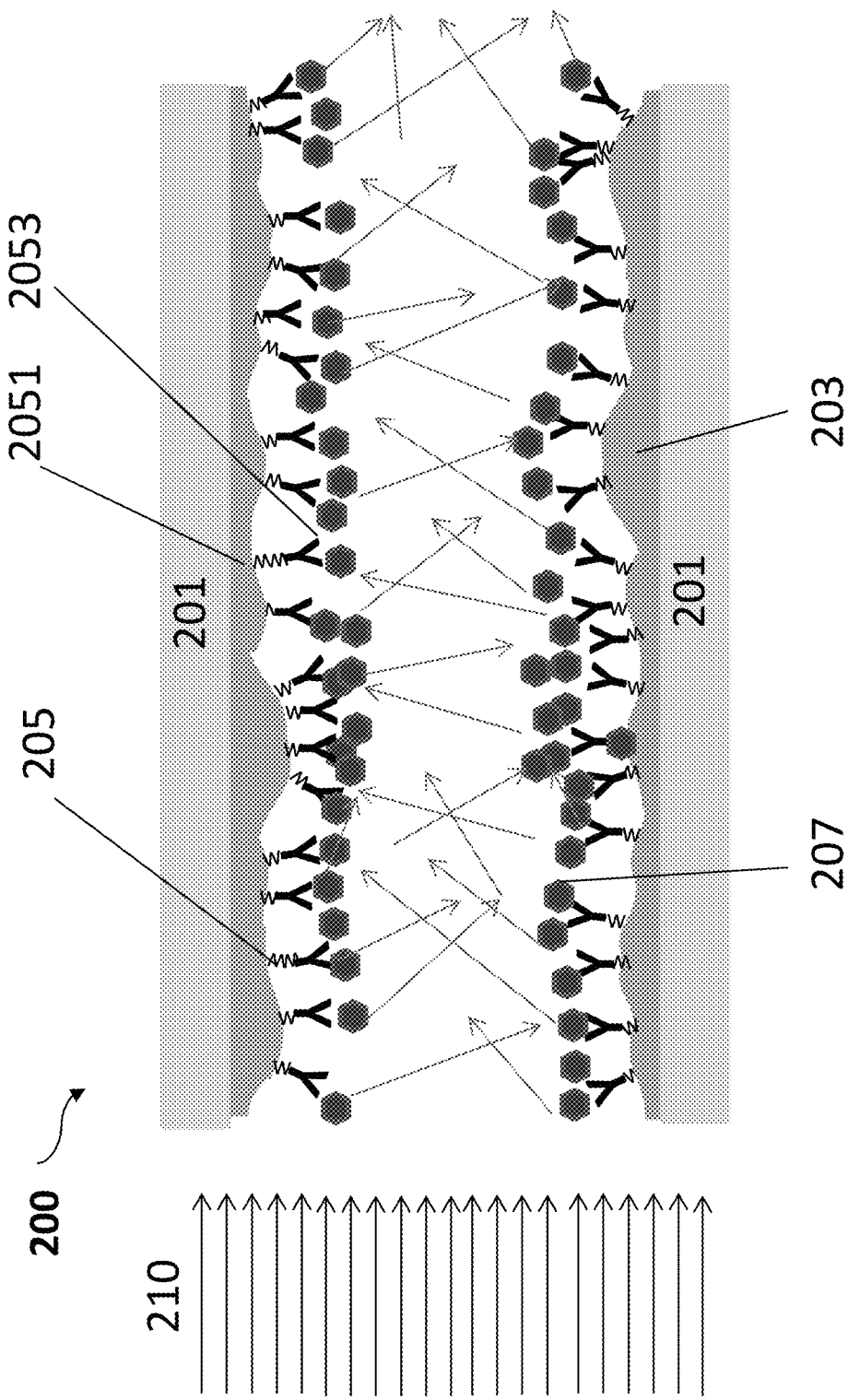
FIG. 2C shows yet another illustrative embodiment of a container of a sensor for detecting a target of interest (e.g., a biomolecule)

FIG. 2C shows an illustrative embodiment of an apparatus for binding a target of interest. The apparatus 200 includes a substrate 201, a film 203 disposed on the substrate and a probe 205 disposed on the film 203. The film 203 has an uneven thickness. In some embodiments, the film may be first coated on the substrate 201 and then annealed to form the uneven thickness. In some embodiments, the thickness of the film 203 may vary from approximately 0.5 nm to approximately 30 nm. A first surface 2051 of the probe 205 is disposed on the film 203. A second surface 2053 of the probe 205 having a binding affinity for the target 207 is configured such that it is available to couple with the target 207 when the target 207 is present. The probes 205 are configured on the material 203 such that light 210 (shown as arrow in FIG. 2C) is scattered when the target 207 binds to the second surface 2053 of probes 205.

Figure 3:
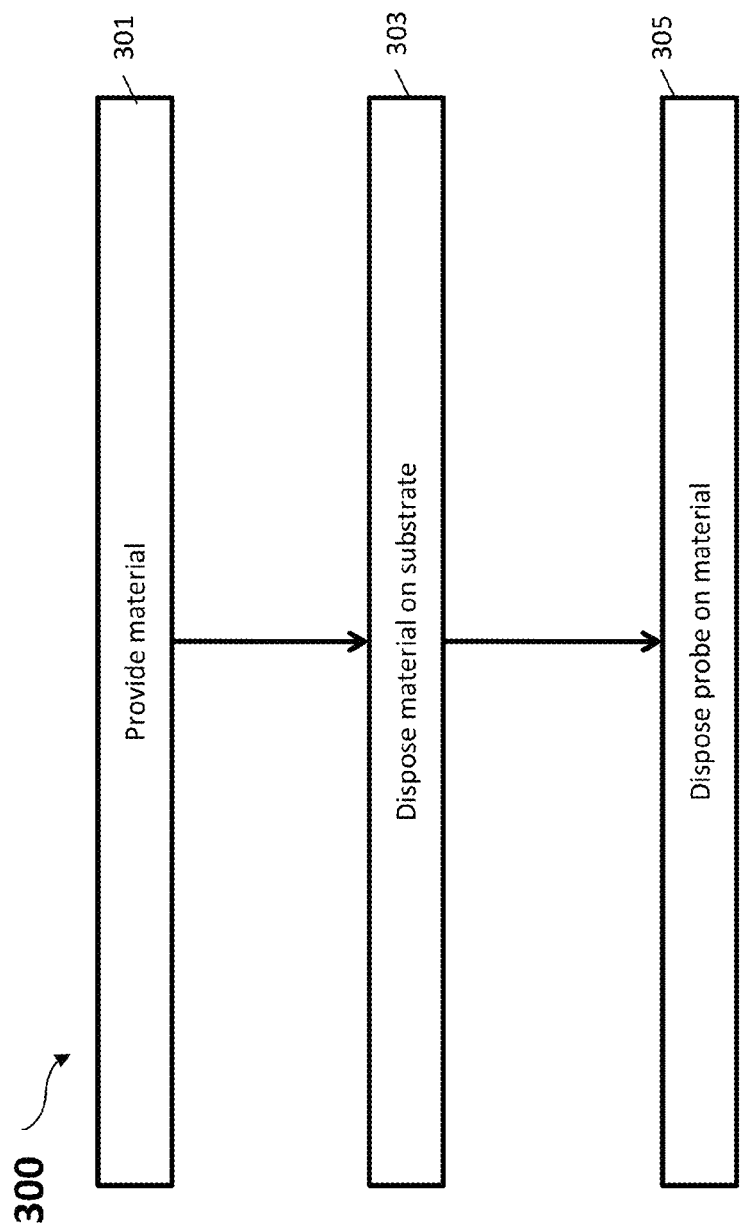
FIG. 3 shows an illustrative embodiment of a method for making a sensor.

FIG. 3 shows a flow chart of an illustrative embodiment of a method 300 for making an apparatus for binding a target of interest. The method 300 includes steps 301, 303 and 305. In step 301, a material is provided. In step 303, the material is disposed on a substrate. The material may be disposed on the substrate in a pattern configured to increase the surface area available for disposing probes, and to permit and/or enhance scattering light emitted from a light source and traveling across the apparatus when a target of interest is bound to a probe that is disposed on the material. The pattern may be, for example, a film, a film with an uneven thickness, or a rod array. In step 305, a probe that is capable of binding to a target of interest is disposed on the material. The probe is configured to interact with the target that the sensor configured to detect. In some embodiments, before disposing the probe on the material, the material may be cleaned and pre-treated. For example, the material may be cleaned with an acidic solution, a basic solution, and/or purified water. In some embodiments, the material may be pre-treated with one or more compounds. In one embodiment, the material may be pretreated with one or more compound(s) that include(s) at least one functional group compatible with the material. In another embodiment, the material may be pretreated with one or more compound(s) that include(s) at least one functional group compatible with the probe. The functional group is configured to form a first stable bound with the free electrons around the surface of the material and form a second stable bound with the probe. Some example functional groups include, but not limited to, thiol group and hydroxyl group.

EXAMPLE 1

[Probe Immobilization]

A glass container configured to contain a sample was placed in a plastic holder and the glass container and the plastic holder were then placed in pTricorder® sensor (Vsense Medtech. Co., Ltd., Taipei, Taiwan). Gold was disposed on an inner surface of the container in the form of a film having an uneven thickness from about 5 nm to about 20 nm. Before introducing probes into the container, the gold film was cleaned with a 0.1M hydrochloric acid solution, purified water, 0.1M sodium hydroxide, and purified water, in sequence.

After cleaning, an aqueous solution containing 110 µL of cystamine (20 mM in phosphate buffered saline (PBS) solution at pH 7.2) was added into the container and incubated for 20 minutes at room temperature to permit cystamine to bind to the gold on the container wall. The remaining cystamine solution was then removed from the container. An aqueous solution containing 110 µL of glutaraldehyde (2.5% in PBS solution at pH 7.2) was then added into the container and incubated for 20 minutes at room temperature to permit glutaraldehyde to bind to the cystamine.

After removing the remaining glutaraldehyde solution from the container, an aqueous solution of 110 µL of commercially available anti-Enterovirus 71 monoclonal antibodies was added into the container and incubated for 20 minutes at room temperature to permit anti-Enterovirus 71 monoclonal antibodies to bind to the glutaraldehyde crosslinker. Unbound anti-Enterovirus 71 monoclonal antibody was then removed from the container by a draining unit of the sensor through a hole at the bottom of the glass container. An aqueous solution of 0.5M glycine was then added to the container to react with residual unbound glutaraldehyde. Finally, glycine was removed from and PBS was added to the container.

[Sample Detection]

Figure 4A:
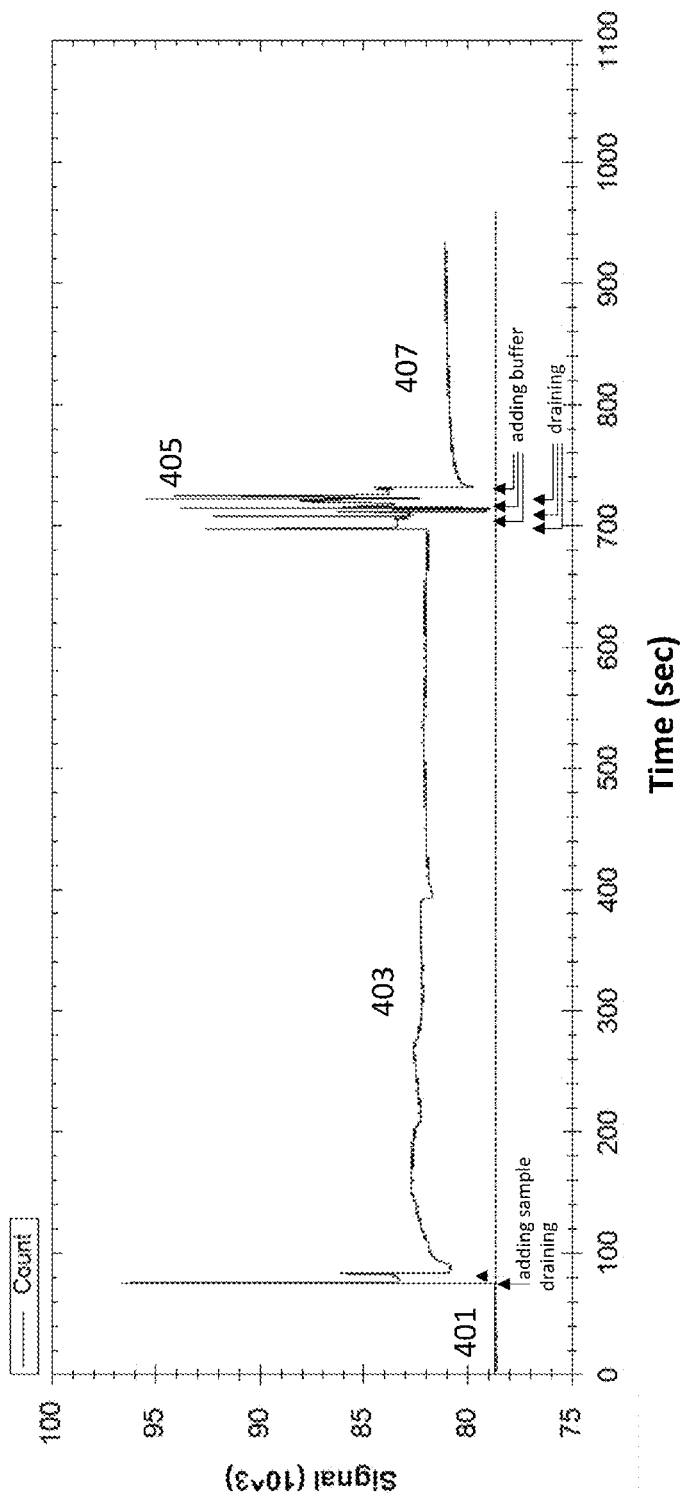
FIG. 4A is a chart illustrating the signal strength during detection, by the sensor, of Enterovirus 71 in a 10% diluted sample collected from an infected patient.

The sensor further includes a visible light source and a light detector for detection of Enterovirus 71. Visible light was transmitted from the visible light source and passed through an optical filter. The optical filter was configured to filter the visible light and only the light having a 560 nm wavelength can pass the optical filter. The light (i.e., having the wavelength of 560 nm) then passed through the glass container set forth above. After passing through the glass container, the light was eventually received by the light detector. FIG. 4A is a chart illustrating the signal strength during detection of Enterovirus 71 in a 10% diluted sample collected from an infected patient. The sample was collected by a throat swab from the infected patient.

The sensor was turned on so that light transmitted from the light source of the sensor passed through the container and over the probes on the inner surface of the container. At this stage, the container contained PBS as set forth above. The signal detected with PBS (as shown at 401 in FIG. 4A) was used as a reference.

After about 1 minute, PBS was removed from the container and the 10% Enterovirus 71 diluted sample was added to the container. Data was collected for 10 minutes. Light detected from the container is shown at 403 in FIG. 4A. After 10 minutes, the Enterovirus 71 diluted sample was removed from the container.

PBS was added to rinse the container to remove nonspecifically bound Enterovirus 71. The rinsing was repeated several times. The rinsing caused various sharp peaks as shown at 405 in FIG. 4A. After rinsing, PBS was added to the container and data was collected for 3 minutes to collect data for light detected from the container (as shown at 407 in FIG. 4A). The difference between the light signal detected at 407 and the signal detected at 401 indicated presence of Enterovirus 71 in the sample.

COMPARATIVE EXAMPLE 1

Figure 4B:
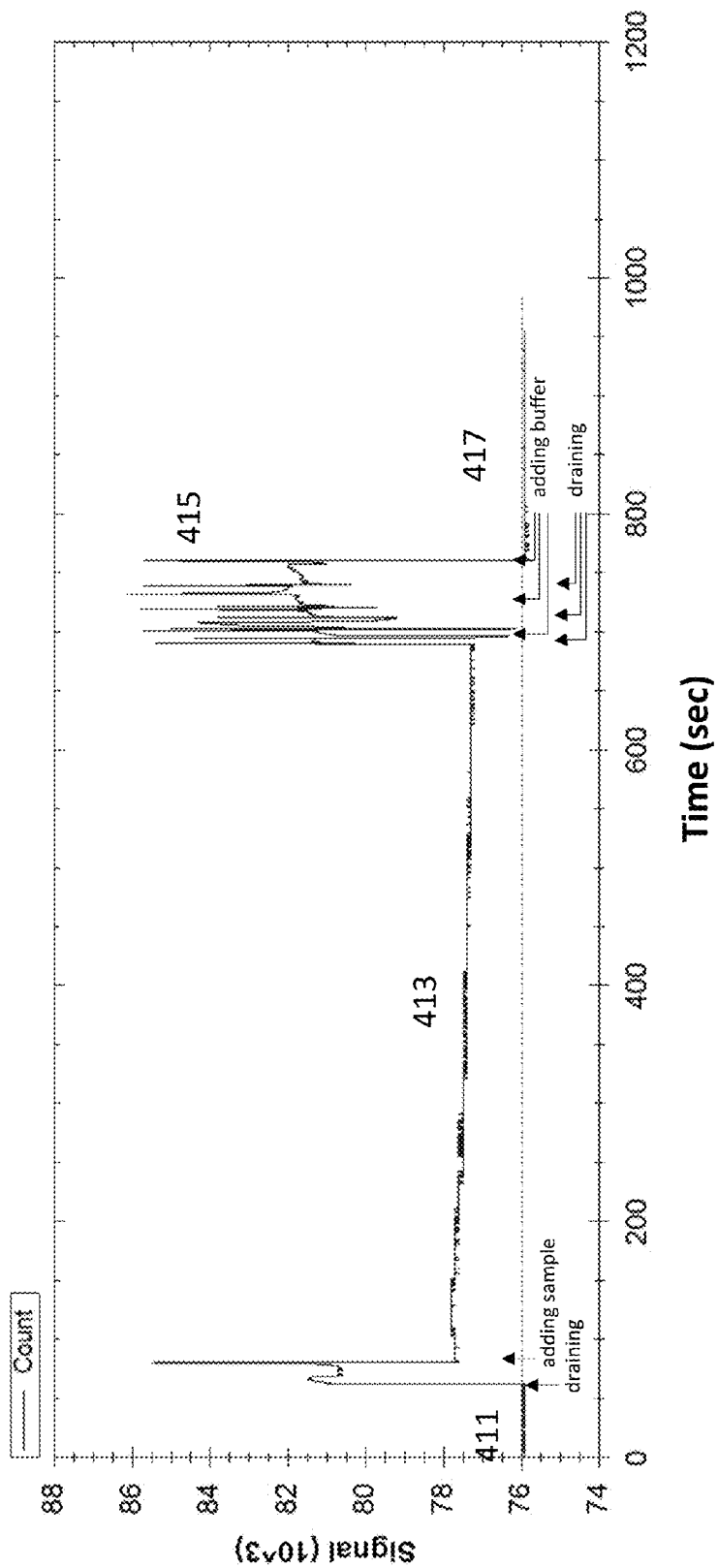
FIG. 4B is a chart illustrating the signal strength during detection, by the sensor, of Enterovirus 71 in a control sample collected from a healthy person.

FIG. 4B is a chart illustrating the signal strength during detection of a control sample collected from a healthy person. The detection approach was the same as the approach of the detection of the 10% Enterovirus 71 diluted sample set forth above.

The sensor was turned on so that a light transmitted from a light source of the sensor passed through the container and over the probes on the inner surface of the container. At this stage, the container contained PBS. The signal detected with PBS (as shown at 411 in FIG. 4B) was used as a reference.

After about 1 minute, PBS was removed from the container and the control sample was added to the container. Data was collected for 10 minutes. Light detected from the container is shown at 413 in FIG. 4B. After 10 minutes, the control sample was removed from the container.

PBS was added to rinse the container to remove nonspecifically bound material. The rinsing was repeated several times. The rinsing caused various sharp peaks as shown at 415 in FIG. 4B. After rinsing, PBS was added to the container and data was collected for 3 minutes to collect data for light detected from the container (as shown at 417 in FIG. 4B). The similar signal strength of 411 and 417 showed no existence of Enterovirus 71 in the control sample.

EXAMPLE 2

[Probe Immobilization]

A glass container configured to contain a sample was placed in a plastic holder and the glass container and the plastic holder were then placed in pTricorder® sensor (Vsense, Medtech, Taipei, Taiwan). Gold was disposed on an inner surface of the container in the form of a film having an uneven thickness from about 5 nm to about 20 nm. Before introducing probes into the container, the gold film was cleaned with a 0.1M hydrochloric acid solution, purified water, 0.1M sodium hydroxide, and purified water, in sequence.

After cleaning, an aqueous solution containing 110 µL of cystamine (20 mM in phosphate buffered saline (PBS) solution at pH 7.2) was added into the container and incubated for 20 minutes at room temperature to permit cystamine to bind to the gold on the container wall. The remaining cystamine solution was then removed from the container. An aqueous solution containing 110 µL of glutaraldehyde (2.5% in PBS solution at pH 7.2) was then added into the container and incubated for 20 minutes at room temperature to permit glutaraldehyde to bind to the cystamine.

After removing the remaining glutaraldehyde solution from the container, an aqueous solution of 110 µL of commercially available anti-Influenza A antibody (20 µg/ml in PBS solution at pH 7.2) was added into the container and incubated for 20 minutes at room temperature to permit the anti-Influenza A antibody to bind to the glutaraldehyde crosslinker. Unbound anti-Influenza A antibody was then removed from the container by a draining unit of the sensor through a hole at the bottom of the glass container. An aqueous solution of 0.5M glycine was then added to the container to react with residual unbound glutaraldehyde. Finally, glycine was removed from and PBS was added to the container.

[Sample Detection]

Figure 5A:
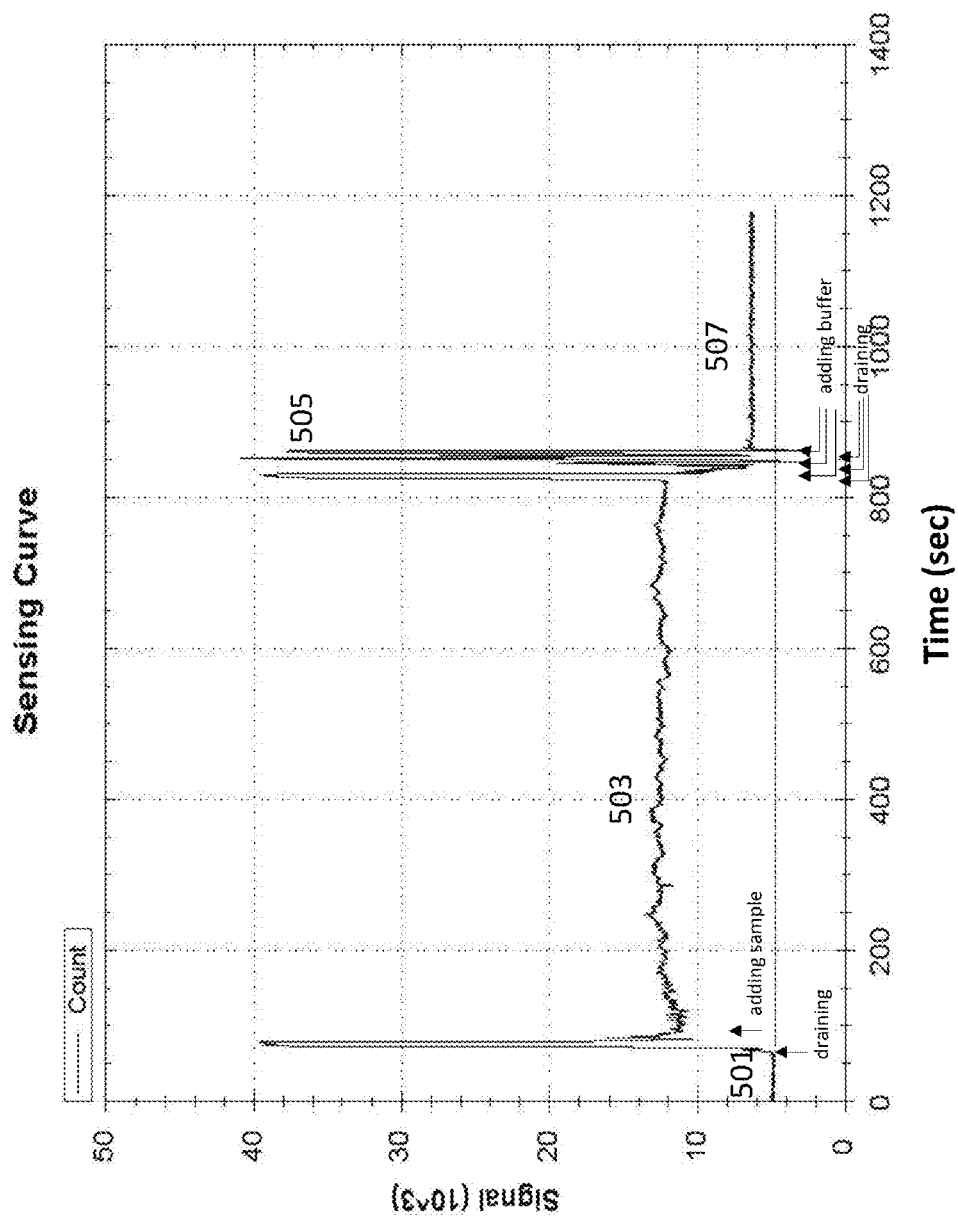
FIG. 5A is a chart illustrating the signal strength during detection, by the sensor, of Influenza A in a 10% diluted sample collected from an infected patient.

The sensor further includes a visible light source and a light detector for detection of Influenza A. Visible light was transmitted from the visible light source and passed through an optical filter. The optical filter was configured to filter the visible light and only the light having a 560 nm wavelength can pass the optical filter. The light (i.e., having the wavelength of 560 nm) then passed through the glass container set forth above. After passing through the glass container, the light was eventually received by the light detector. FIG. 5A is a chart illustrating the signal strength during detection of Influenza A in a 10% diluted sample collected from an infected patient. The sample was collected by a throat swab from the infected patient's throat.

The sensor was turned on so that light transmitted from a light source of the sensor passed through the container and over the probes on the inner surface of the container. At this stage, the container contained PBS as set forth above. The signal detected with PBS (as shown at 501 in FIG. 5A) was used as a reference.

After about 1 minute, PBS was removed from the container and the 10% Influenza A diluted sample was added to the container. Data was collected for 10 minutes. Light detected from the container is shown at 503 in FIG. 5A. After 10 minutes, the Influenza A diluted sample was removed from the container.

PBS was added to rinse the container to remove nonspecifically bound material. The rinsing was repeated several times. The rinsing caused various sharp peaks as shown at 505 in FIG. 5A. After rinsing, PBS was added to the container and data was collected for 3 minutes to collect data for light detected from the container (as shown at 507 in FIG. 5A). The difference between the light signal detected at 507 and the signal detected at 501 indicated presence of Influenza A in the sample.

COMPARATIVE EXAMPLE 2

Figure 5B:
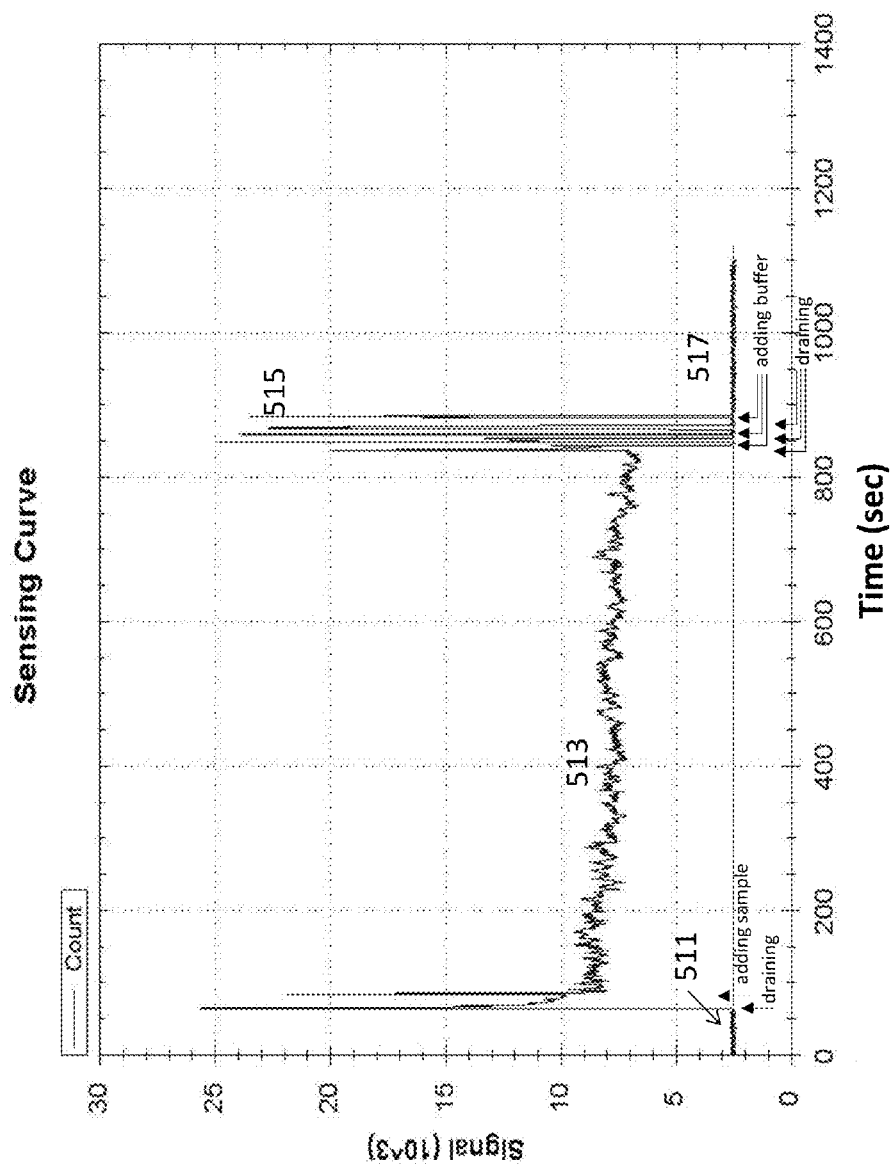
FIG. 5B is a chart illustrating the signal strength during detection, by the sensor, of influenza A in a control sample collected from a healthy person.
Figure 6A:
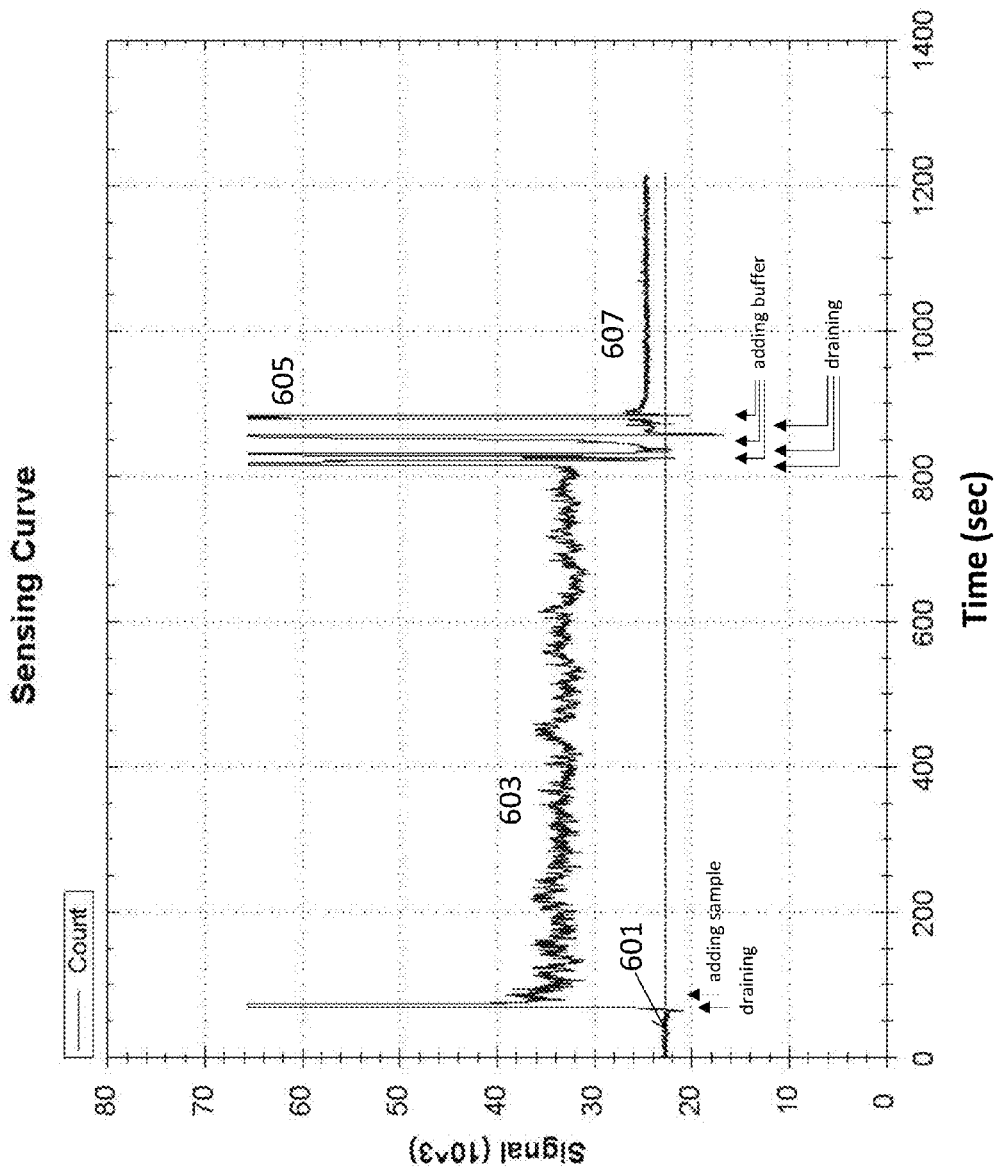
FIG. 6A is a chart illustrating the signal strength during detection, by the sensor, of Influenza B in a 10% diluted sample collected from an infected patient.
Figure 9:
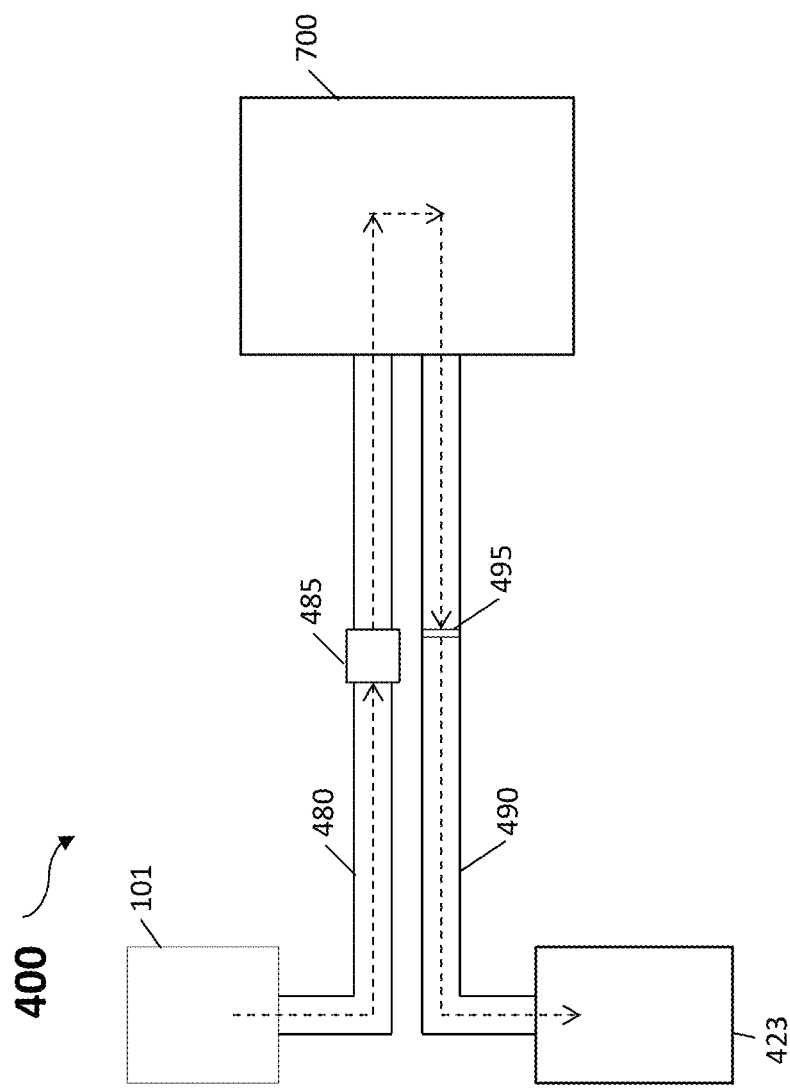
FIG. 9 shows yet another illustrative embodiment of a draining unit of a sensor for detecting a target of interest (e.g., a biomolecule)

FIG. 5B is a chart illustrating the signal strength during detection of a control sample collected from a healthy person. The detection approach was the same as the approach of the detection of the Influenza A diluted sample set forth above.

The sensor was turned on so that a light transmitted from a light source of the sensor passed through the container and over the probes on the inner surface of the container. At this stage, the container contained PBS. The signal detected with PBS (as shown at 511 in FIG. 5B) was used as a reference.

After about 1 minute, PBS was removed from the container and the control sample was added to the container. Data was collected for 10 minutes. Light detected from the container is shown at 513 in FIG. 5B. After 10 minutes, the control sample was removed from the container.

PBS was added to rinse the container to remove nonspecifically bound material. The rinsing was repeated several times. The rinsing caused various sharp peaks as shown at 515 in FIG. 5B. After rinsing, PBS was added to the container and data was collected for 3 minutes to collect data for light detected from the container (as shown at 517 in FIG. 5B). The similar signal strength of 511 and 517 showed no existence of Influenza A in the control sample.

EXAMPLE 3

[Probe Immobilization]

A glass container configured to contain a sample was placed in a plastic holder and the glass container and the plastic holder were then placed in pTricorder® sensor (Vsense Medtech Taipei, Taiwan). Gold was disposed on an inner surface of the container in the form of a film having an uneven thickness from about 5 nm to about 20 nm. Before introducing probes into the container, the gold film was cleaned with a 0.1M hydrochloric acid solution, purified water, 0.1M sodium hydroxide, and purified water, in sequence.

After cleaning, an aqueous solution containing 110 µL of cystamine (20 mM in phosphate buffered saline (PBS) solution at pH 7.2) was added into the container and incubated for 20 minutes at room temperature to permit cystamine to bind to the gold on the container wall. The remaining cystamine solution was then removed from the container. An aqueous solution containing 110 µL of glutaraldehyde (2.5% in PBS solution at pH 7.2) was then added into the container and incubated for 20 minutes at room temperature to permit glutaraldehyde to bind to the cystamine.

After removing the remaining glutaraldehyde solution from the container, an aqueous solution of 110 µL of commercially available anti-Influenza B antibody (20 µg/ml in PBS solution at pH 7.2) was added into the container and incubated for 20 minutes at room temperature to permit the anti-Influenza B antibody to bind to the glutaraldehyde crosslinker. Unbound anti-Influenza B antibody was then removed from the container by a draining unit of the sensor through a hole at the bottom of the glass container. An aqueous solution of 0.5M glycine was then added to the container to react with residual unbound glutaraldehyde. Finally, glycine was removed from and PBS was added to the container.

[Sample Detection]

The sensor further includes a visible light source and a light detector for detection of Influenza B. Visible light was transmitted from the visible light source and passed through an optical filter. The optical filter was configured to filter the visible light and only the light having a 560 nm wavelength can pass the optical filter. The light (i.e., having the wavelength of 560 nm) then passed through the glass container set forth above. After passing through the glass container, the light was eventually received by the light detector. FIG. 6A is a chart illustrating the signal strength during detection of Influenza B in a 10% diluted sample collected from an infected patient. The sample was collected by a throat swab from the infected patient's throat.

The sensor was turned on so that light transmitted from a light source of the sensor passed through the container and over the probes on the inner surface of the container. At this stage, the container contained PBS as set forth above. The signal detected with PBS (as shown at 601 in FIG. 6A) was used as a reference.

After about 1 minute, PBS was removed from the container and the 10% Influenza B diluted sample was added to the container. Data was collected for 10 minutes. Light detected from the container is shown at 603 in FIG. 6A. After 10 minutes, the Influenza B diluted sample was removed from the container.

PBS was added to rinse the container to remove nonspecifically bound material. The rinsing was repeated several times. The rinsing caused various sharp peaks as shown at 605 in FIG. 6A. After rinsing, PBS was added to the container and data was collected for 3 minutes to collect data for light detected from the container (as shown at 607 in FIG. 6A). The difference between the light signal detected at 607 and the signal detected at 601 indicated presence of Influenza B in the sample.

COMPARATIVE EXAMPLE 3

FIG. 6B is a chart illustrating the signal strength during detection of a control sample collected from a healthy person. The detection approach was the same as the approach of the detection of the Influenza B diluted sample set forth above.

The sensor was turned on so that a light transmitted from a light source of the sensor passed through the container and over the probes on the inner surface of the container. At this stage, the container contained PBS. The signal detected with PBS (as shown at 611 in FIG. 6B) was used as a reference.

After about 1 minute, PBS was removed from the container and the control sample was added to the container. Data was collected for 10 minutes. Light detected from the container is shown at 613 in FIG. 6B. After 10 minutes, the control sample was removed from the container.

PBS was added to rinse the container to remove nonspecifically bound material. The rinsing was repeated several times. The rinsing caused various sharp peaks as shown at 615 in FIG. 6B. After rinsing, PBS was added to the container and data was collected for 3 minutes to collect data for light detected from the container (as shown at 617 in FIG. 6B). The similar signal strength of 611 and 617 showed no existence of Influenza B in the control sample.

FIGS. 7A and 7B show the top view and the front view of an illustrative embodiment of a draining unit 400 of a sensor for detecting a target of interest (e.g., a biomolecule), respectively. The draining unit 400 may include a closed chamber 410. The chamber 410 may comprise at least a first opening 420 configured to form an airtight connection to a pump 423 and a second opening 430 configured to form an airtight connection to the second hole 108 of the container 101. The first opening 420 and the second opening 430 are formed on opposite walls of the chamber 410 and are offset from one another so that the two openings 420 and 430 do not overlap. The pump 423 connected to the first opening 420 may be configured to suck liquid out from the container 101 though the second opening 430.

In some embodiments, the pump 423 is configured to generate suction for sucking air in the container 101 into the chamber 410 through the second opening 430, and then toward the pump 423 through the first opening 420. As air flows from the container 101 to the pump 423, liquid in the container 101 is sucked into the chamber 410 through the second opening 430, and is drained into a waste collecting unit via a third opening 450. The chamber 410 further includes a blocking unit 440 between the first opening 420 and the second opening 430. The blocking unit 440 may extend from the wall comprising the second opening 430 towards the opposite wall, so as to prevent liquid flowing into the chamber 410 from being sucked into the pump 423.

FIGS. 8A and 8B show the top view and side view of another illustrative embodiment of a draining unit of a sensor for detecting a target of interest (e.g., a biomolecule), respectively. The draining unit 400 may include a chamber 410. The chamber 410 may comprise at least a first opening 420 configured to form an airtight connection with a pump 423 and a second opening 430 configured to form an airtight connection with the second hole 108 of the container 101. The first opening 420 and the second opening 430 may be formed on the same or different walls of the chamber 410.

A third opening 460 may be formed on a wall of the chamber 410, and the draining unit 400 may further include a first tube 470 for connecting the chamber 410, via the third opening 460, with a waste collecting unit 700. Furthermore, the draining unit 400 may include a second tube 435 connected to the second opening 430 from within the chamber 410, and extends towards the waste collecting unit 700 from within the first tube 470. The second tube 435 may have a smaller diameter than that of the first tube 470. The pump 423 connected to the first opening 420 may be configured to suck liquid out from the container 101 though the second opening 430.

In some embodiments, air (shown as an arrow in FIG. 8A and FIG. 8B) in the container 101 may flow into the second tube 435 via the second opening 430, into the chamber 410 via at least the first tube 470, and toward the pump 423 via the first opening 420. As air flows from the container 101 to the pump 423, liquid in the container 101 is also sucked into the second tube 435 through the second opening 430, and is drained into the waste collecting unit 700. The second tube 435 that drains the liquid from the container 101 into the waste collecting unit 700 may prevent liquid from being sucked into the pump 423.

FIG. 9 shows yet another illustrative embodiment of a draining unit 400 of a sensor for detecting a target of interest (e.g., a biomolecule). The draining unit 400 may include a first tube 480 with one end connected to a waste collecting unit 700 and the other end configured to form an air tight connection with the second hole 108 of the container 101 of the sensor. The draining unit 400 may further include a second tube 490 with one end connect to the waste collecting unit 700 and the other end configured to form an air tight connection with a pump 423.

Air (shown as an arrow in FIG. 9) in the container 101 may flow into the waste collecting unit 700 via the first tube 480 and then toward the pump 423 via the second tube 490. As air flows from the container 101 to the pump 423, liquid in the container 101 is also sucked into the waste collecting unit 700 via the first tube 480, but does not get sucked into the second tube 490. The draining unit 400 may further include a valve 485 disposed in the path of the first tube 480, and is configured to allow liquid and air to flow in the direction indicated by the arrow, but not in the opposite direction, so as to prevent backflow of liquid in the waste collecting unit 700.

In addition, a water blocking unit 495 may be disposed in the second tube 490, configured to allow air to flow from the waste collecting unit 700 to the pump 423, while preventing water and vapor in the waste collecting unit 700 from going into the pump 423. The water blocking unit 495 may comprise a waterproof and breathable membrane, such as a hydrophobic microporous polymer membrane comprising polyurethane (PU), polytetrafluoroethylene (PTFE), expanded polytetrafluoroethylene (ePTFE) or ePTFE with PU. Examples of commercially available waterproof and breathable fabric may include, but is not limited to, MemBrain® by Marmot (PU), POWERTEX® by Salewa (PU), EFMaflon® by EMF (PTFE), gore tex performance Shell™ by GORE-TEX® (ePTFE) or eVent Direct Venting™ by eVent (ePTFE with PU).

EXAMPLE 4

[Probe Immobilization]

A container configured to contain a sample was placed in a plastic holder and the container and the plastic holder were then placed in pTricorder® sensor (Vsense Medtech. Co., Ltd., Taipei, Taiwan). Gold was disposed on an inner surface of the container in the form of a film having a thickness of approximately 100 nm Before introducing probes into the container, the gold film was cleaned with a 0.1M hydrochloric acid solution, distilled water, 0.1M sodium hydroxide, and distilled water, in sequence.

After cleaning, an aqueous solution containing 110 µL of cystamine (20 mM in phosphate buffered saline (PBS) solution at pH 7.2) was added into the container and incubated for 20 minutes at room temperature to permit cystamine to bind to the gold film on the container wall. The remaining cystamine solution was then removed from the container. An aqueous solution containing 110 µL of glutaraldehyde (2.5% in PBS solution at pH 7.2) was then added into the container and incubated for 20 minutes at room temperature to permit glutaraldehyde to bind to the cystamine.

After removing the remaining glutaraldehyde solution from the container, an aqueous solution of 110 µL of commercially available anti-Enterovirus type 71 monoclonal antibodies was added into the container and incubated for 20 minutes at room temperature to permit anti-Enterovirus type 71 monoclonal antibodies to bind to the glutaraldehyde crosslinker. Unbound anti-Enterovirus type 71 monoclonal antibody was then removed from the container by a draining unit of the sensor as shown in FIGS. 7A and 7B through a hole at the bottom of the container. An aqueous solution of 0.5M glycine was then added to the container to react with residual unbound glutaraldehyde. Finally, glycine was removed from and PBS was added to the container.

[Sample Detection]

Figure 10A:
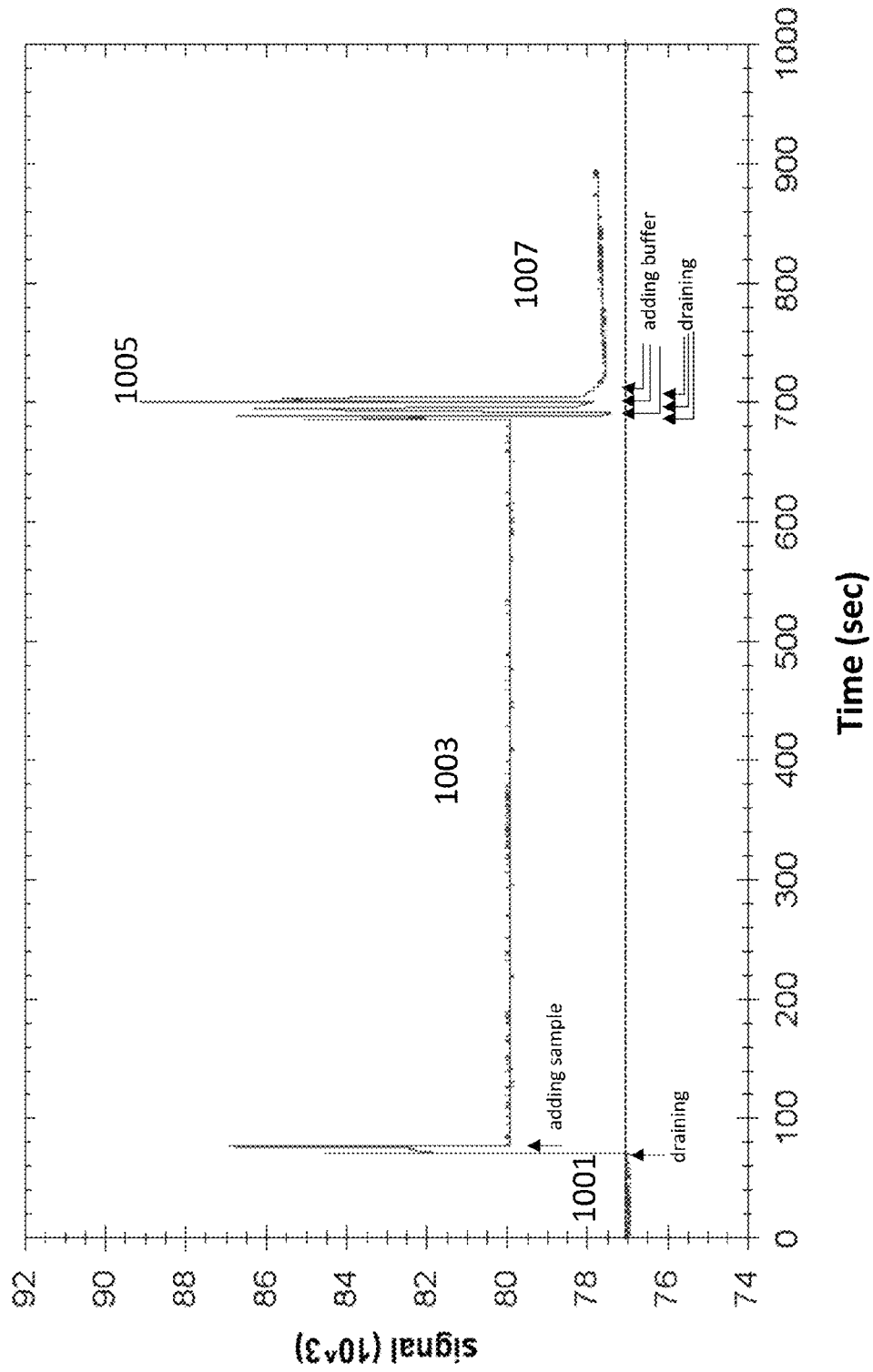
FIG. 10A is a chart illustrating the signal strength during a sensor, which comprises a pump illustrated in FIGS. 7A and 7B, detecting a 10% diluted Enterovirus type 71-containing sample collected from an infected patient.

The sensor further includes a visible light source and a light detector for detection of Enterovirus type 71. Visible light was transmitted from the visible light source and passed through an optical filter. The optical filter was configured to filter the visible light and only the light having a 560 nm wavelength can pass the optical filter. The light (i.e., having the wavelength of 560 nm) then passed through the container set forth above. After passing through the container, the light was eventually received by the light detector. FIG. 10A is a chart illustrating the signal strength during detection of Enterovirus type 71 in a 10% diluted sample collected from an infected patient. The sample was collected by a throat swab from the infected patient.

The sensor was turned on so that light transmitted from a light source of the sensor passed through the container and over the probes on the inner surface of the container. At this stage, the container contained PBS as set forth above. The signal detected with PBS (as shown at 1001 in FIG. 10A) was used as a reference.

After about 1 minute, PBS was removed from the container and the 10% diluted Enterovirus type 71-containing sample was added to the container followed by interaction with the probe. Data was collected for 10 minutes. Light detected from the container is shown at 1003 in FIG. 10A. After 10 minutes, the Enterovirus type 71-containing sample was removed from the container.

PBS was added to rinse the container to remove nonspecifically bound Enterovirus type 71 and other impurities. The rinsing was repeated several times. The rinsing caused various sharp peaks as shown at 1005 in FIG. 10A. After rinsing, PBS was added to the container and data was collected for 3 minutes to collect data for light detected from the container (as shown at 1007 in FIG. 10A). The difference between the light signal detected at 1007 and the signal detected at 1001 indicated presence of Enterovirus type 71 in the sample.

COMPARATIVE EXAMPLE 4

Figure 10B:
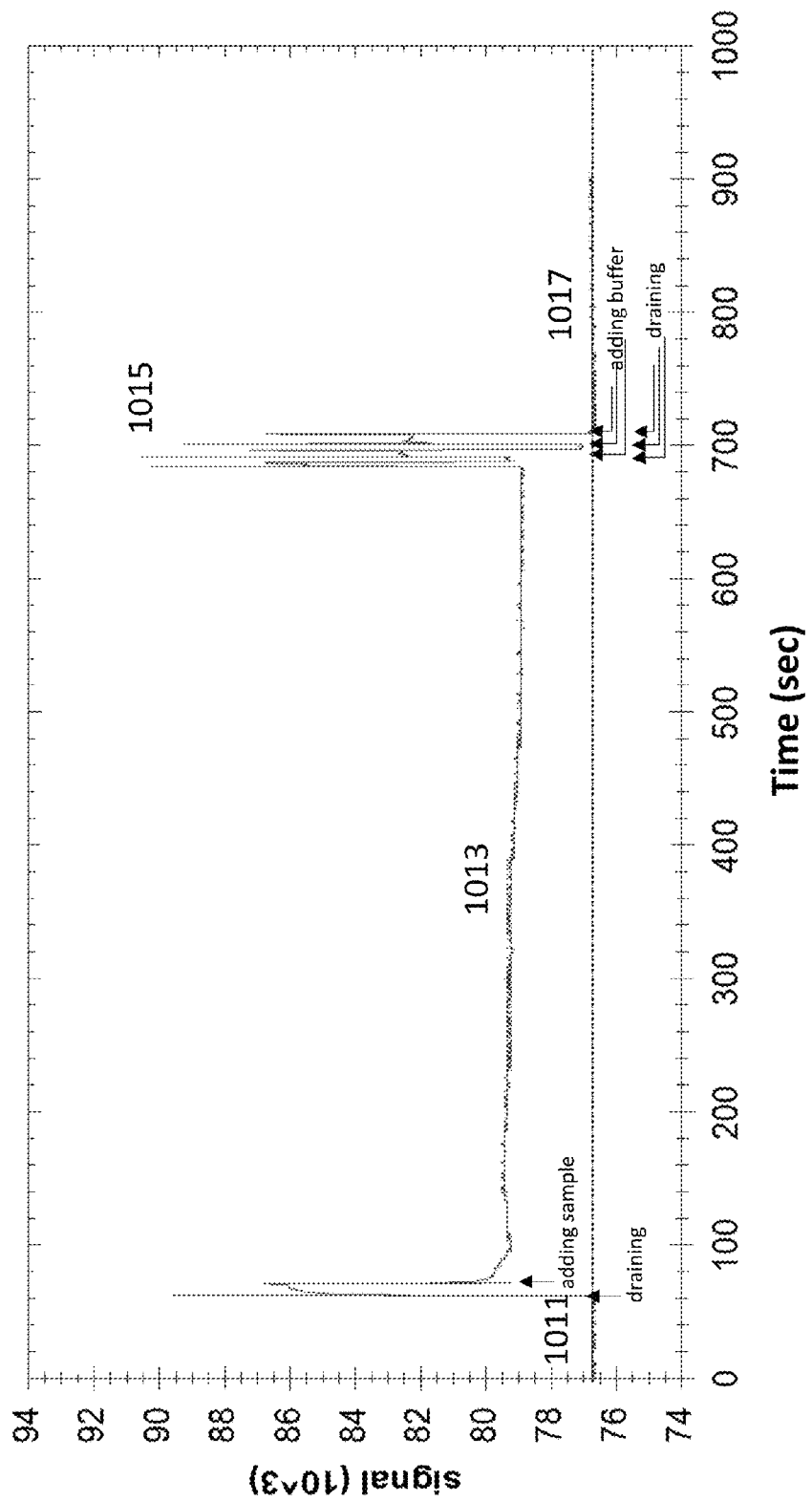
FIG. 10B is a chart illustrating the signal strength during a sensor, which comprises a pump illustrated in FIGS. 7A and 7B, detecting a control sample collected from a healthy person.
Figure 11A:
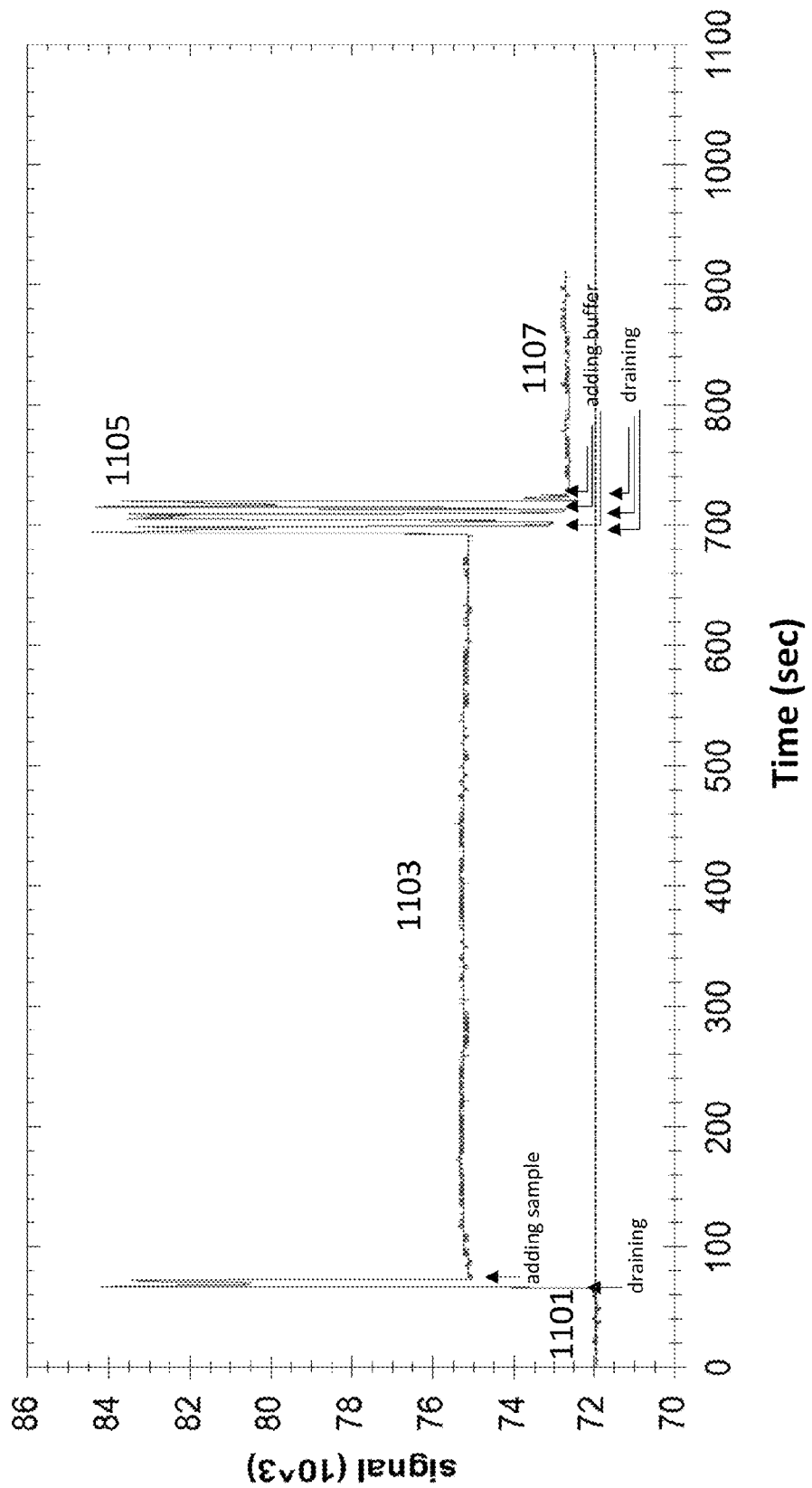
FIG. 11A is a chart illustrating the signal strength during a sensor, which comprises a pump illustrated in FIGS. 8A and 8B, detecting a 10% diluted Enterovirus type 71-containing sample collected from an infected patient.
Figure 11B:
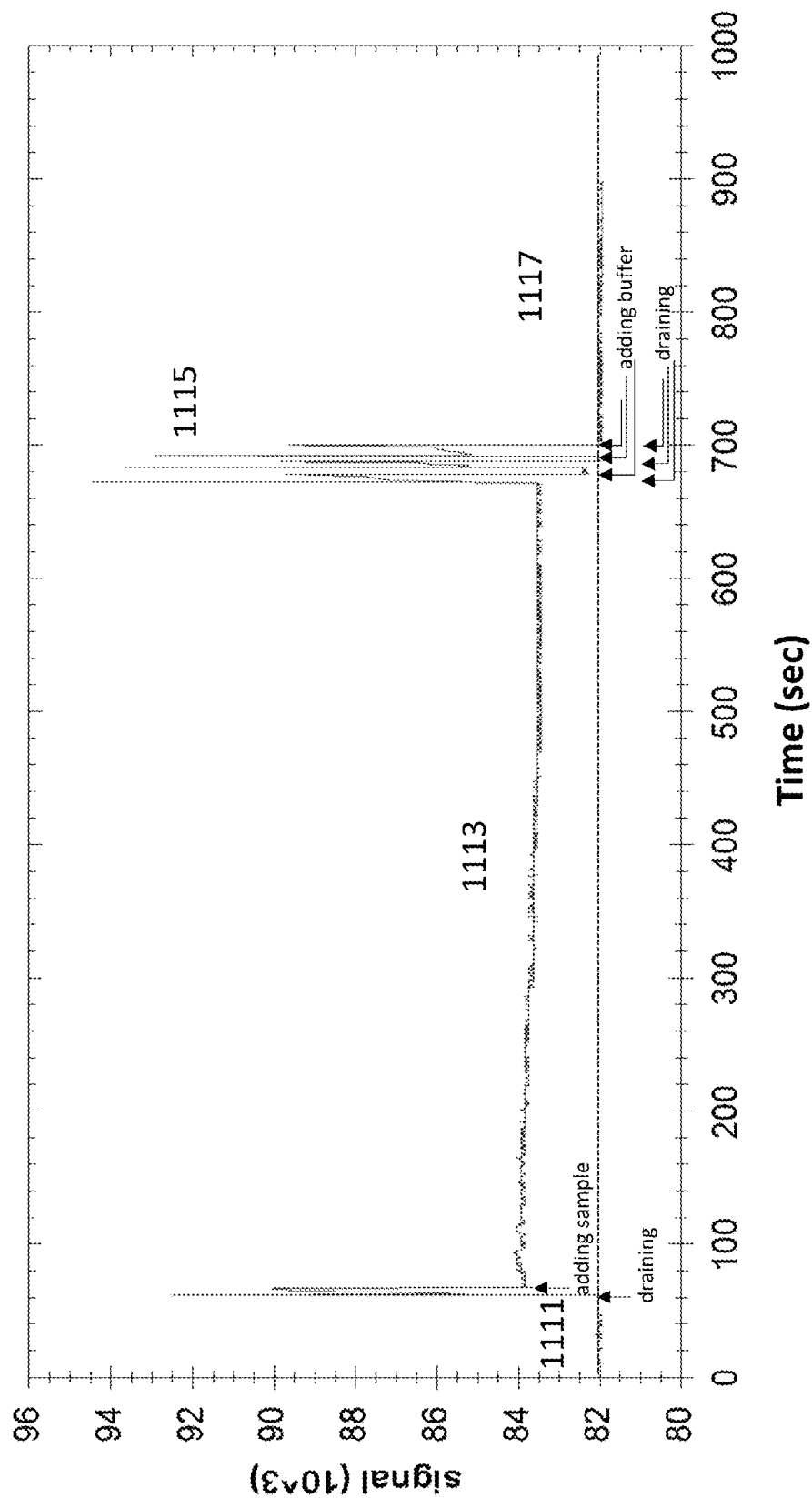
FIG. 11B is a chart illustrating the signal strength during a sensor, which comprises a pump illustrated in FIGS. 8A and 8B, detecting a control sample collected from a healthy person.
Figure 12A:
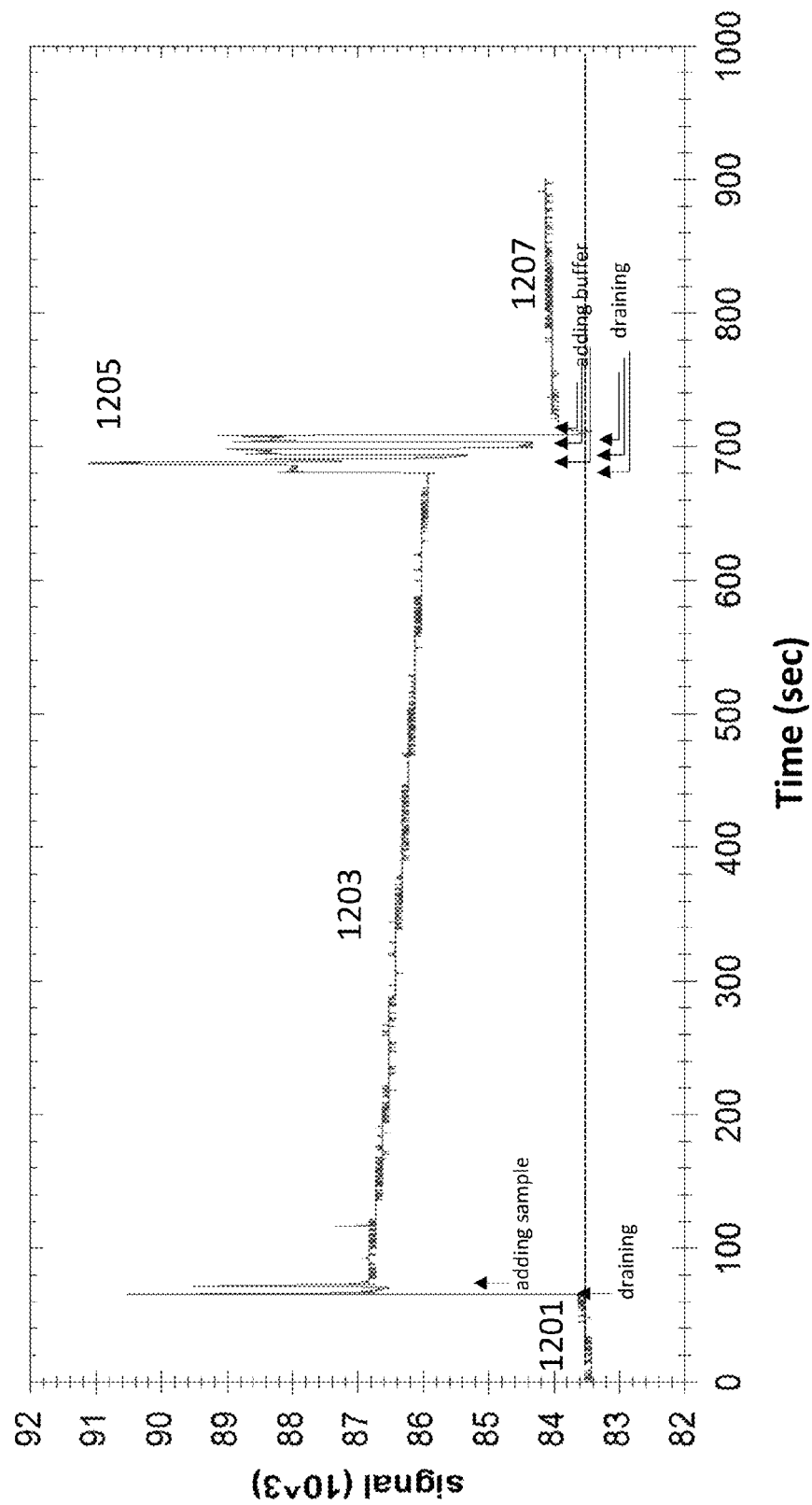
FIG. 12A is a chart illustrating the signal strength during a sensor, which comprises a pump illustrated in FIG. 9, detecting a 10% diluted Enterovirus type 71-containing sample collected from an infected patient.
Figure 12B:
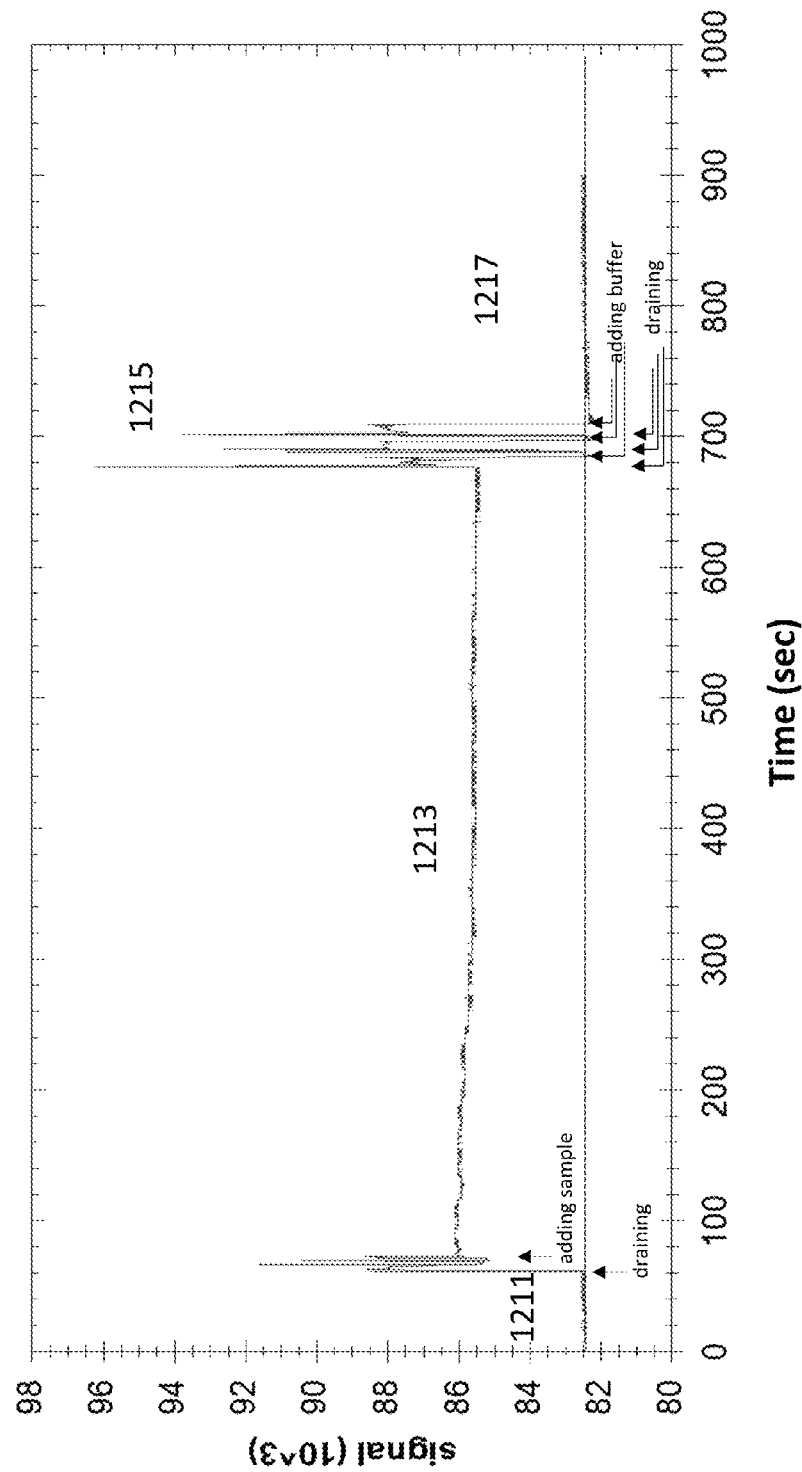
FIG. 12B is a chart illustrating the signal strength during a sensor, which comprises a pump illustrated in FIG. 9, detecting a control sample collected from a healthy person, all arranged in accordance with embodiments of the disclosure.

FIG. 10B is a chart illustrating the signal strength during detection of a control sample collected from a healthy person. The detection approach was the same as the approach of the detection of the 10% diluted Enterovirus type 71-containing sample set forth above.

The sensor was turned on so that a light transmitted from a light source of the sensor passed through the container and over the probes on the inner surface of the container. At this stage, the container contained PBS. The signal detected with PBS (as shown at 1011 in FIG. 10B) was used as a reference.

After about 1 minute, PBS was removed from the container and the control sample was added to the container. Data was collected for 10 minutes. Light detected from the container is shown at 1013 in FIG. 10B. After 10 minutes, the control sample was removed from the container.

PBS was added to rinse the container to remove nonspecifically bound material. The rinsing was repeated several times. The rinsing caused various sharp peaks as shown at 1015 in FIG. 10B. After rinsing, PBS was added to the container and data was collected for 3 minutes to collect data for light detected from the container (as shown at 1017 in FIG. 10B). The similar signal strength of 1011 and 1017 showed no existence of Enterovirus type 71 in the control sample.

EXAMPLE 5

[Probe Immobilization]

A container configured to contain a sample was placed in a plastic holder and the container and the plastic holder were then placed in pTricorder® sensor (Vsense Medtech. Co., Ltd., Taipei, Taiwan). Gold was disposed on an inner surface of the container in the form of a film having an uneven thickness which varies from approximately 0.5 nm to approximately 30 nm. Before introducing probes into the container, the gold film was cleaned with a 0.1M hydrochloric acid solution, distilled water, 0.1M sodium hydroxide, and distilled water, in sequence.

After cleaning, an aqueous solution containing 110 µL of cystamine (20 mM in phosphate buffered saline (PBS) solution at pH 7.2) was added into the container and incubated for 20 minutes at room temperature to permit cystamine to bind to the gold film on the container wall. The remaining cystamine solution was then removed from the container. An aqueous solution containing 110 µL of glutaraldehyde (2.5% in PBS solution at pH 7.2) was then added into the container and incubated for 20 minutes at room temperature to permit glutaraldehyde to bind to the cystamine.

After removing the remaining glutaraldehyde solution from the container, an aqueous solution of 110 µL of commercially available anti-Enterovirus 71 monoclonal antibodies was added into the container and incubated for 20 minutes at room temperature to permit anti-Enterovirus 71 monoclonal antibodies to bind to the glutaraldehyde crosslinker. Unbound anti-Enterovirus 71 monoclonal antibody was then removed from the container by a draining unit of the sensor as shown in FIGS. 8A and 8B through a hole at the bottom of the container. An aqueous solution of 0.5M glycine was then added to the container to react with residual unbound glutaraldehyde. Finally, glycine was removed from and PBS was added to the container.

[Sample Detection]

The sensor further includes a visible light source and a light detector for detection of Enterovirus type 71. Visible light was transmitted from the visible light source and passed through an optical filter. The optical filter was configured to filter the visible light and only the light having a 560 nm wavelength can pass the optical filter. The light (i.e., having the wavelength of 560 nm) then passed through the glass container set forth above. After passing through the glass container, the light was eventually received by the light detector. FIG. 11A is a chart illustrating the signal strength during detection of Enterovirus 71 in a 10% diluted Enterovirus type 71-containing sample collected from an infected patient. The sample was collected by a throat swab from the infected patient.

The sensor was turned on so that light transmitted from a light source of the sensor passed through the container and over the probes on the inner surface of the container. At this stage, the container contained PBS as set forth above. The signal detected with PBS (as shown at 1101 in FIG. 11A) was used as a reference.

After about 1 minute, PBS was removed from the container and the 10% diluted Enterovirus type 71-containing sample was added to the container. Data was collected for 10 minutes. Light detected from the container is shown at 1103 in FIG. 11A. After 10 minutes, the sample was removed from the container.

PBS was added to rinse the container to remove nonspecifically bound Enterovirus type 71 and other impurities. The rinsing was repeated several times. The rinsing caused various sharp peaks as shown at 1105 in FIG. 11A. After rinsing, PBS was added to the container and data was collected for 3 minutes to collect data for light detected from the container (as shown at 1107 in FIG. 11A). The difference between the light signal detected at 1107 and the signal detected at 1101 indicated presence of Enterovirus type 71 in the sample.

COMPARATIVE EXAMPLE 5

FIG. 11B is a chart illustrating the signal strength during detection of a control sample collected from a healthy person. The detection approach was the same as the approach of the detection of the 10% diluted Enterovirus type 71-containing sample set forth above.

The sensor was turned on so that a light transmitted from a light source of the sensor passed through the container and over the probes on the inner surface of the container. At this stage, the container contained PBS. The signal detected with PBS (as shown at 1111 in FIG. 11B) was used as a reference.

After about 1 minute, PBS was removed from the container and the control sample was added to the container. Data was collected for 10 minutes. Light detected from the container is shown at 1113 in FIG. 11B. After 10 minutes, the control sample was removed from the container.

PBS was added to rinse the container to remove nonspecifically bound material. The rinsing was repeated several times. The rinsing caused various sharp peaks as shown at 1115 in FIG. 11B. After rinsing, PBS was added to the container and data was collected for 3 minutes to collect data for light detected from the container (as shown at 1117 in FIG. 11B). The similar signal strength of 1111 and 1117 showed no existence of Enterovirus type 71 in the control sample.

EXAMPLE 6

[Probe Immobilization]

A container configured to contain a sample was placed in a plastic holder and the container and the plastic holder were then placed in pTricorder® sensor (Vsense Medtech. Co., Ltd., Taipei, Taiwan). Gold was disposed on an inner surface of the container in the form of a film having a pattern of a rod array. A rod of the rod array has a length of approximately 500 nm, a width of approximately 500 nm and a height of approximately 100 nm, and each rod is spaced apart from another rod by approximately 500 nm. Before introducing probes into the container, the gold film was cleaned with a 0.1M hydrochloric acid solution, distilled water, 0.1M sodium hydroxide, and distilled water, in sequence.

After cleaning, an aqueous solution containing 110 μL of cystamine (20 mM in phosphate buffered saline (PBS) solution at pH 7.2) was added into the container and incubated for 20 minutes at room temperature to permit cystamine to bind to the gold film on the container wall. The remaining cystamine solution was then removed from the container. An aqueous solution containing 110 μL of glutaraldehyde (2.5% in PBS solution at pH 7.2) was then added into the container and incubated for 20 minutes at room temperature to permit glutaraldehyde to bind to the cystamine.

After removing the remaining glutaraldehyde solution from the container, an aqueous solution of 110 μL of commercially available anti-Enterovirus type 71 monoclonal antibodies was added into the container and incubated for 20 minutes at room temperature to permit anti-Enterovirus type 71 monoclonal antibodies to bind to the glutaraldehyde crosslinker. Unbound anti-Enterovirus type 71 monoclonal antibody was then removed from the container by a draining unit of the sensor as shown in FIG. 9 through a hole at the bottom of the container. An aqueous solution of 0.5M glycine was then added to the container to react with residual unbound glutaraldehyde. Finally, glycine was removed from and PBS was added to the container.

[Sample Detection]

The sensor further includes a visible light source and a light detector for detection of Enterovirus type 71. Visible light was transmitted from the visible light source and passed through an optical filter. The optical filter was configured to filter the visible light and only the light having a 560 nm wavelength can pass the optical filter. The light (i.e., having the wavelength of 560 nm) then passed through the container set forth above. After passing through the container, the light was eventually received by the light detector. FIG. 12A is a chart illustrating the signal strength during detection of Enterovirus type 71 in a 10% diluted sample collected from an infected patient. The sample was collected by a throat swab from the infected patient.

The sensor was turned on so that light transmitted from a light source of the sensor passed through the container and over the probes on the inner surface of the container. At this stage, the container contained PBS as set forth above. The signal detected with PBS (as shown at 1201 in FIG. 12A) was used as a reference.

After about 1 minute, PBS was removed from the container and the 10% diluted Enterovirus type 71-containing sample was added to the container followed by interaction with the probe. Data was collected for 10 minutes. Light detected from the container is shown at 1203 in FIG. 12A. After 10 minutes, the Enterovirus type 71-containing sample was removed from the container.

PBS was added to rinse the container to remove nonspecifically bound Enterovirus type 71 and other impurities. The rinsing was repeated several times. The rinsing caused various sharp peaks as shown at 1205 in FIG. 12A. After rinsing, PBS was added to the container and data was collected for 3 minutes to collect data for light detected from the container (as shown at 1207 in FIG. 12A). The difference between the light signal detected at 1207 and the signal detected at 1201 indicated presence of Enterovirus type 71 in the sample.

COMPARATIVE EXAMPLE 6

FIG. 12B is a chart illustrating the signal strength during detection of a control sample collected from a healthy person. The detection approach was the same as the approach of the detection of the 10% diluted Enterovirus type 71-containing sample set forth above.

The sensor was turned on so that a light transmitted from a light source of the sensor passed through the container and over the probes on the inner surface of the container. At this stage, the container contained PBS. The signal detected with PBS (as shown at 1211 in FIG. 12B) was used as a reference.

After about 1 minute, PBS was removed from the container and the control sample was added to the container. Data was collected for 10 minutes. Light detected from the container is shown at 1213 in FIG. 12B. After 10 minutes, the control sample was removed from the container.

PBS was added to rinse the container to remove nonspecifically bound material. The rinsing was repeated several times. The rinsing caused various sharp peaks as shown at 1215 in FIG. 12B. After rinsing, PBS was added to the container and data was collected for 3 minutes to collect data for light detected from the container (as shown at 1217 in FIG. 12B). The similar signal strength of 1211 and 1217 showed no existence of Enterovirus type 71 in the control sample.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A sensor for detecting a target of interest comprising:
an apparatus for binding the target of interest, the apparatus comprising:
a substrate;
a material disposed on the substrate; and
a probe disposed on the material and configured to bind to the target of interest, wherein the probe is configured on the material to scatter light emitted from a light source when the target of interest is bound to the probe; and
a draining unit for draining fluid from the apparatus, comprises:
a first opening for connecting with a pump;
a second opening for connecting with an outlet of the apparatus, wherein the pump is configured to generate suction for sucking air out of the apparatus, into a chamber of the draining unit and then toward the pump and wherein the first and the second opening are formed on opposite walls of the chamber and are offset from one another; and
a blocking unit between the first opening and the second opening, wherein the blocking unit extends from the wall comprising the second opening towards the wall comprising the first opening.

2. The sensor of claim 1, wherein the chamber further comprises:
a drain hole for draining fluid from the chamber into a waste collecting unit.

3. The sensor of claim 1, wherein the draining unit further comprises:
a chamber comprising the first opening and the second opening;
a first tube for connecting the chamber with a waste collecting unit; and
a second tube inside the chamber extending from the second opening and into the first tube.

4. The sensor of claim 1, wherein the draining unit further comprises:
a first tube for connecting the apparatus with the waste collecting unit; and
a second tube for connecting the pump and the waste collecting unit.

5. The sensor of claim 4, wherein the draining unit further comprises:
a backflow blocking unit set within the first tube and configured to allow air and liquid to flow from the apparatus to the waste collecting unit, and to block liquid to flow from the waste collecting unit to the apparatus.

6. The sensor of claim 5, wherein the backflow blocking unit comprises a valve.

7. The sensor of claim 4, wherein the draining unit further comprises:
a water blocking unit set within the second tube and configured to allow air to flow from the waste collecting unit to the pump, and to block water from the waste collecting unit to enter the pump.

8. The sensor of claim 7, wherein the water blocking unit comprises a waterproof and breathable polymer membrane.

9. The sensor of claim 8, wherein the polymer membrane comprises a hydrophobic microporous polymer membrane comprising at least one of polyurethane (PU), polytetrafluoroethylene (PTFE) and expanded polytetrafluoroethylene (ePTFE).

10. The sensor of claim 1, wherein the probe comprises DNA, RNA, a protein, an antibody, an antibody fragment, an aptamer, an antigen, or an epitope.

11. The sensor of claim 1, wherein the target of interest is a biomolecule.

12. The sensor of claim 1, wherein the target comprises a virus, a protein, a nucleic acid, a carbohydrate, a lipid, a hapten, or a toxin.

13. The sensor of claim 1, wherein the probe binds to the target of interest with an affinity of about 100 piconewtons to about 500 piconewtons.

14. The sensors of claim 1, wherein the material comprises a metal.

15. The sensor of claim 1, wherein the material comprises a pattern configured to scatter light emitted from the light source.

16. The sensor of claim 1, wherein the material comprises a film on the substrate.

17. The sensor of claim 16, wherein a substantially even thickness is in the range of 5 nm to 200 nm or the uneven thickness varies from 0.5 nm to 30 nm.

18. The sensor of claim 1, wherein the material comprises a rod array disposed on the substrate.

19. The sensor of claim 18, wherein the size of a rod in the rod array is associated with the size of the probe and a size of a target of interest which the probe is configured to bind to.

20. The sensor of claim 18, wherein a rod of the rod array has a length from 200 to 900 nm, a width from 200 to 900 nm and a height from 15 to 1500 nm.

21. The sensor of claim 1 further comprising:
a light source that emits light;
a light receiver for receiving the light emitted from the light source and scattered by the probe when the target of interest is bound to the probe; and
a detector configured to generate an electrical signal, the magnitude of which reflects the amount of the light emitted from the light source and scattered by the probe when the target of interest is bound to the probe that is received by the light receiver,
wherein the apparatus is located between the light source and the light receiver, and
wherein the apparatus is configured such that the probe is in the path of the light emitted by the light source.

22. The sensor of claim 21, wherein the light emitted from the light source comprises a wavelength of about 200 nm to about 800 nm.

* * * * *